US008883954B2

(12) United States Patent
Byrne et al.

(10) Patent No.: US 8,883,954 B2
(45) Date of Patent: Nov. 11, 2014

(54) PHOTOACTIVE POLYMERS

(71) Applicant: Merck Patent GmbH, Darmstadt (DE)

(72) Inventors: Paul Byrne, Morristown, PA (US); Li Wen, Woodbury, MN (US); David P. Waller, Lexington, MA (US); Taizoon Canteenwala, Lowell, MA (US); Patrick Foyle, Somerville, MA (US); Edward Jackson, Mansfield, MA (US)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 14/049,536

(22) Filed: Oct. 9, 2013

(65) Prior Publication Data

US 2014/0053905 A1 Feb. 27, 2014

Related U.S. Application Data

(63) Continuation of application No. PCT/US2012/035254, filed on Apr. 26, 2012.

(60) Provisional application No. 61/479,934, filed on Apr. 28, 2011.

(51) Int. Cl.
*C08G 65/38* (2006.01)
*H01L 51/42* (2006.01)
*C07F 7/08* (2006.01)
*C07D 495/04* (2006.01)
*C07D 513/04* (2006.01)
*B82Y 10/00* (2011.01)
*C07D 417/14* (2006.01)
*C08G 61/12* (2006.01)
*H01L 51/00* (2006.01)

(52) U.S. Cl.
CPC ............ *H01L 51/0068* (2013.01); *H01L 51/42* (2013.01); *H01L 51/0053* (2013.01); *C08G 2261/364* (2013.01); *C08G 2261/1412* (2013.01); *C07F 7/0816* (2013.01); *C07D 495/04* (2013.01); *H01L 51/0071* (2013.01); *C07D 513/04* (2013.01); *B82Y 10/00* (2013.01); *C07D 417/14* (2013.01); *C08G 2261/91* (2013.01); *H01L 51/0036* (2013.01); *C08G 61/123* (2013.01); *C08G 2261/414* (2013.01); *H01L 51/4246* (2013.01); *H01L 51/0094* (2013.01); *H01L 51/0043* (2013.01); *C08G 2261/124* (2013.01); *Y02E 10/549* (2013.01); *H01L 51/0047* (2013.01); *H01L 51/4253* (2013.01); *C08G 2261/3246* (2013.01)
USPC ............ 528/216; 528/255; 528/94; 528/289; 528/377; 528/380; 526/240; 526/257; 549/4; 548/126

(58) Field of Classification Search
USPC .................. 528/216, 255, 94, 289, 377, 380; 526/240, 257; 549/4; 548/126; 136/263
See application file for complete search history.

(56) References Cited

U.S. PATENT DOCUMENTS

2008/0087324 A1  4/2008  Gaudiana et al.

FOREIGN PATENT DOCUMENTS

| WO | 2008067023 | 6/2008 |
| WO | 2012149189 | 4/2012 |

OTHER PUBLICATIONS

Morkved E.H. et al., "Preparations and Template Cyclotetramerisations of 2, 1, 3-Benzothia (selena) diazole-5, 6-dicarbonit riles," Acta Chemica Scandinavica, Munksgaard, Copenhagen, DK, vol. 49, Jan. 1, 1995, pp. 658-662, XP002580517, ISSN: 0904-213X, the whole document.
Written Opinion of the International Searching Authority, PCT Application No. PCT/US2012/035254.
International Search Report, PCT Application No. PCT/US2012/035254.
International Preliminary Report on Patentability, PCT Application No. PCT/US2012/035254.

*Primary Examiner* — Shane Fang
(74) *Attorney, Agent, or Firm* — Bowditch & Dewey, LLP; Roger P. Zimmerman

(57) ABSTRACT

A photovoltaic cell is provided that includes a first electrode, a second electrode, and a photoactive layer disposed between the first and second electrodes. The photoactive layer includes a photoactive polymer containing a first monomer repeat unit, which contains a moiety of formula (1):

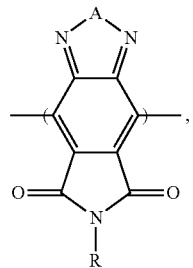

(1)

in which A and R are defined in the specification.

44 Claims, 3 Drawing Sheets

PHOTOACTIVE POLYMERS

CROSS REFERENCE TO RELATED APPLICATION

This application is a continuation of and claims the benefit of co-pending international patent application PCT/US2012/035254, filed Apr. 26, 2012, and claims the benefit of U.S. Provisional Application Ser. No. 61/479,934, filed Apr. 28, 2011, under 35 U.S.C. §119(e); the contents of both applications are hereby incorporated by reference.

TECHNICAL FIELD

This disclosure relates to novel photoactive polymers, as well as related monomers, articles, systems, and methods.

BACKGROUND

Photovoltaic cells are commonly used to transfer energy in the form of light into energy in the form of electricity. A typical photovoltaic cell includes a photoactive material disposed between two electrodes. Generally, light passes through one or both of the electrodes to interact with the photoactive material, thereby generating charge carriers (i.e., electrons and holes). As a result, the ability of the photoactive material to absorb light and general charge carriers can limit the overall efficiency of a photovoltaic cell.

SUMMARY

This disclosure is based on the unexpected discovery that a photovoltaic cell that includes a polymer containing a pyrrolo[3,4-f]-2,1,3-benzothiadiazole-5,7-dione moiety in a photoactive layer can have a significantly improved energy conversion efficiency.

In one aspect, this disclosure features a photoactive polymer that includes a first monomer repeat unit containing a moiety of formula (1):

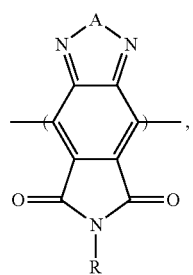

(1)

in which A is O, S, or Se; and R is H, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl.

In another aspect, this disclosure features an article that includes a first electrode, a second electrode, and a photoactive layer disposed between the first and second electrodes. The photoactive layer includes a photoactive polymer described above. The article is configured as a photovoltaic cell.

In another aspect, this disclosure features a compound of formula (69):

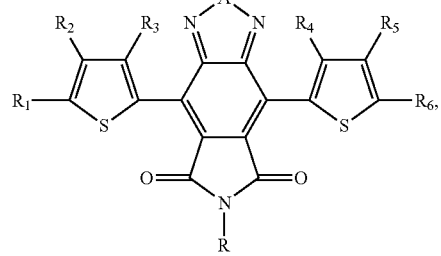

(69)

in which A is O, S, or Se; R is H, $C_1$-$C_{24}$ alkyl optionally containing oxygen, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl; and each of $R_1$, $R_2$, $R_3$, $R_4$, $R_5$, and $R_6$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$, each $R_c$ independently, being H, $C_1$-$C_{24}$ alkyl, aryl, heteroaryl, $C_3$-$C_{24}$ cycloalkyl, or $C_3$-$C_{24}$ heterocycloalkyl.

In still another aspect, this disclosure features a compound of formula (70):

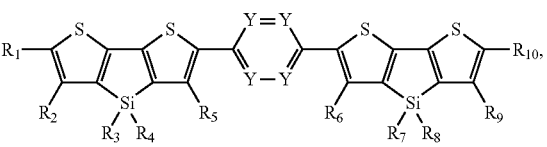

(70)

in which each Y, independently, is N or $C(R_a)$, each $R_a$, independently, being H, halo, $C_1$-$C_{24}$ alkyl, aryl, heteroaryl, $C_3$-$C_{24}$ cycloalkyl, or $C_3$-$C_{24}$ heterocycloalkyl; and each of $R_1$, $R_2$, $R_3$, $R_4$, $R_5$, $R_6$, $R_7$, $R_8$, $R_9$, and $R_{10}$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_{ca}$, each $R_c$ independently, being H, $C_1$-$C_{24}$ alkyl, aryl, heteroaryl, $C_3$-$C_{24}$ cycloalkyl, or $C_3$-$C_{24}$ heterocycloalkyl.

Other features, objects, and advantages of the subject matter in this disclosure will be apparent from the description and drawings, and from the claims.

DESCRIPTION OF DRAWINGS

Like reference symbols in the various drawings indicate like elements.

DETAILED DESCRIPTION

Figure 1:
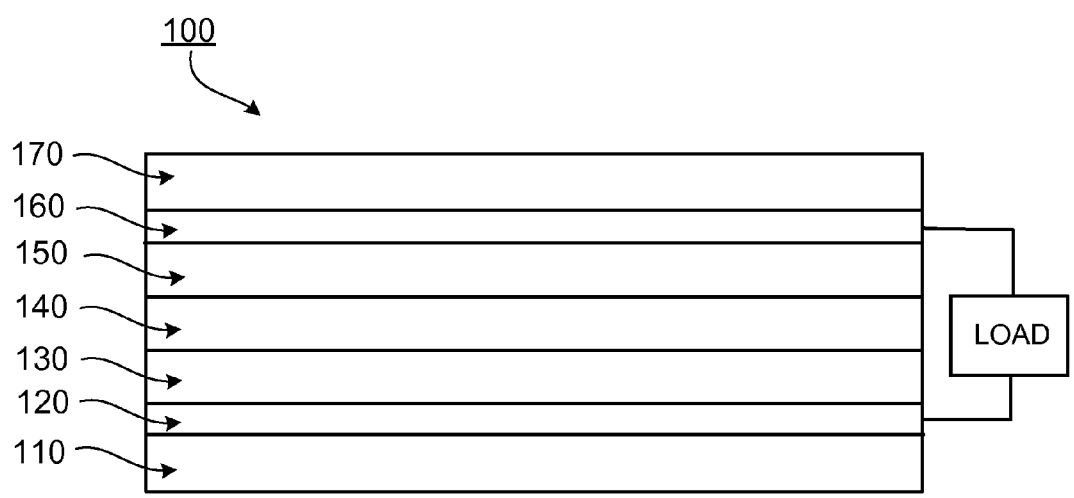
FIG. 1 is a cross-sectional view of an embodiment of a photovoltaic cell.

FIG. 1 shows a cross-sectional view of a photovoltaic cell 100 that includes a substrate 110, an electrode 120, an optional hole blocking layer 130, a photoactive layer 140 (e.g., containing an electron acceptor material and an electron donor material), a hole carrier layer 150, an electrode 160, and a substrate 170.

In general, during use, light can impinge on the surface of substrate 110, and passes through substrate 110, electrode 120, and optional hole blocking layer 130. The light then interacts with photoactive layer 140, causing electrons to be transferred from the electron donor material (e.g., a photoactive polymer described herein) to the electron acceptor material (e.g., a substituted fullerene). The electron acceptor material then transmits the electrons through optional hole blocking layer 130 to electrode 120, and the electron donor material transfers holes through hole carrier layer 150 to electrode 160. Electrodes 120 and 160 are in electrical connection via an external load so that electrons pass from electrode 120 through the load to electrode 160.

In some embodiments, the electron donor or acceptor material in photoactive layer 140 can include one or more polymers (e.g., copolymers). A polymer mentioned herein includes at least two identical or different monomer repeat units (e.g., at least 5 monomer repeat units, at least 10 monomer repeat units, at least 50 monomer repeat units, at least 100 monomer repeat units, or at least 500 monomer repeat units). A copolymer mentioned herein refers to a polymer that includes at least two (e.g., three, four, five, or six) monomer repeat units having different chemical structures. In general, the polymers suitable for use as electron donor or acceptor materials are photovoltaically active.

In some embodiments, the electron donor material can include a photoactive polymer containing a first monomer repeat unit that includes a moiety of formula (1):

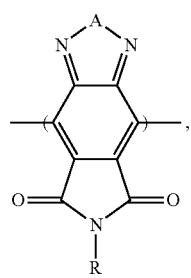

(1)

in which A is O, S, or Se; and R is H, $C_1$-$C_{24}$ alkyl optionally containing oxygen, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl. For example, in the moiety of formula (1), A can be S and R can be $C_1$-$C_{24}$ alkyl (e.g., $C_8H_{17}$, $C_{12}H_{25}$, or $C_{20}H_{41}$) optionally substituted with halo or $C_1$-$C_{24}$ alkoxy.

An alkyl, alkenyl, and alkynyl can be branched or straight chained. A $C_1$-$C_{24}$ alkyl contains any of 1 to 24 carbon atoms. A $C_2$-$C_{24}$ alkenyl or $C_2$-$C_{24}$ alkynyl contains any of 2 to 24 carbon atoms. Examples of alkyl moieties include —$CH_3$, and branched —$C_3H_7$. Examples of alkenyl moieties include —$CH_2$=$CH_2$—$CH_3$, —$CH_2$—$CH$=$CH_2$, and —$CH_2$=$CH_2$—$CH(CH_3)_2$. Examples of alkynyl moieties include —C≡C—$CH_3$, —$CH_2$—C≡CH, and —C≡C—$CH(CH_3)_2$.

An alkoxy can be branched or straight chained. A $C_1$-$C_{24}$ alkoxy contains an oxygen radical and any of 1 to 24 carbon atoms. Examples of alkoxy moieties include —$OCH_3$ and —$OCH_2CH(CH_3)_2$.

A cycloalkyl can contain one or more (e.g., two, three, four, or five) saturated rings. A cycloalkenyl can contain one or more (e.g., two, three, four, or five) rings in which at least one ring contains at least one double bond. A $C_3$-$C_{24}$ cycloalkyl or $C_3$-$C_{24}$ cycloalkenyl contains any of 3 to 24 carbon atoms. An example of a cycloalkyl moiety is cyclohexyl. An example of a cycloalkenyl moiety is cyclohexenyl.

A heterocycloalkyl can contain one or more (e.g., two, three, four, or five) saturated rings. A heterocycloalkenyl can contain one or more (e.g., two, three, four, or five) rings in which at least one ring contains at least one double bond. A $C_3$-$C_{24}$ heterocycloalkyl or $C_3$-$C_{24}$ heterocycloalkenyl contains at least one ring heteroatom (e.g., O, N, and S) and any of 3 to 24 carbon atoms. An example of a heterocycloalkyl moiety is 4-tetrahydropyranyl. An example of a heterocycloalkenyl moiety is 4-pyranyl.

An aryl can contain one or more (e.g., two, three, four, or five) aromatic rings. Examples of aryl moieties include phenyl, naphthyl, naphthylene, pyrenyl, anthryl, and phenanthryl. A heteroaryl can contain one or more (e.g., two, three, four, or five) aromatic rings, at least one of which contains at least one ring heteroatom (e.g., O, N, and S). Examples of heteroaryl moieties include furyl, fluorenyl, pyrrolyl, thienyl, oxazolyl, imidazolyl, thiazolyl, pyridyl, pyrimidinyl, quinazolinyl, quinolyl, isoquinolyl, and indolyl.

Alkyl, alkenyl, alkynyl, alkoxy, cycloalkyl, cycloalkenyl, heterocycloalkyl, heterocycloalkenyl, aryl, and heteroaryl mentioned herein include both substituted and unsubstituted moieties, unless specified otherwise. Examples of substituents on cycloalkyl, cycloalkenyl, heterocycloalkyl, heterocycloalkenyl, aryl, and heteroaryl include $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, $C_1$-$C_{24}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halo (e.g., F, Cl, Br, or I), thio, $C_1$-$C_{10}$ alkylthio, arylthio, $C_1$-$C_{10}$ alkylsulfonyl, arylsulfonyl, cyano, nitro, acyl, acyloxy, carboxyl, and carboxylic ester. Examples of substituents on alkyl, alkenyl, alkynyl, and alkoxy include all of the above-recited substituents except $C_1$-$C_{20}$ alkyl. Cycloalkyl, cycloalkenyl, heterocycloalkyl, heterocycloalkenyl, aryl, and heteroaryl also include fused groups.

Without wishing to be bound by theory, it is believed that a photoactive polymer containing a moiety of formula (1) (e.g., a pyrrolo[3,4-f]-2,1,3-benzothiadiazole-5,7-dione moiety) can have an appropriate LUMO and HOMO values. As a result, such a photoactive polymer can be incorporated in a photoactive layer of a photovoltaic cell to produce a photovoltaic cell having a significantly improved energy conversion efficiency.

In some embodiments, the photoactive polymer described herein can have a LUMO value of at most about –3.8 eV (e.g., at most about –3.9 eV or at most about –4 eV) when measured against a vacuum potential of –4.7 eV. Without wishing to be bound by theory, it is believed that, if the photoactive polymer has a LUMO value higher than –3.8 eV, the photoactive polymer could have a relatively large bandgap (e.g., larger than 1.6 eV), which would reduce the efficiency of the photovoltaic cell made from this polymer.

In some embodiments, the photoactive polymer can further include a second monomer repeat unit different from the first monomer repeat unit. The second monomer repeat unit can be either an electron donating moiety or an electron accepting moiety. In some embodiments, the second monomer repeat unit can be a moiety selected from the group consisting of the moieties of formulas (2)-(23):
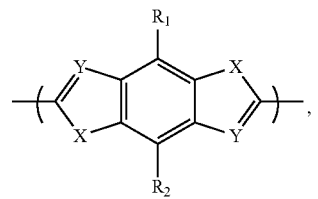
(2)
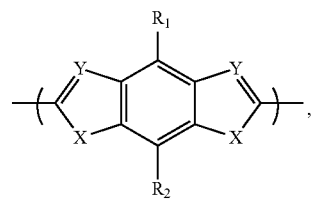
(3)
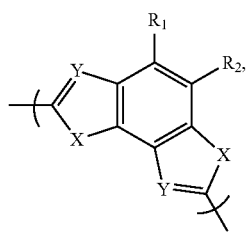
(4)
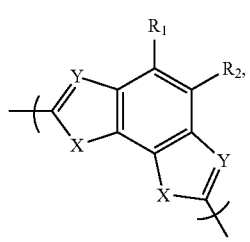
(5)
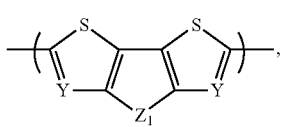
(6)
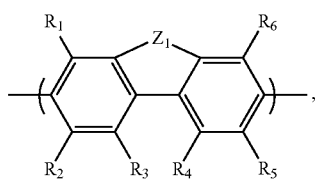
(7)
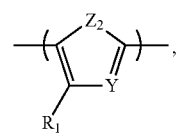
(8)
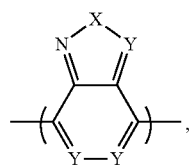
(9)
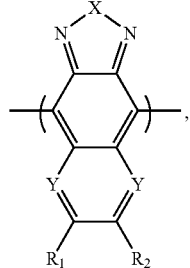
(10)
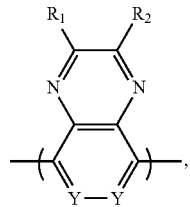
(11)
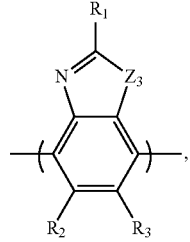
(12)
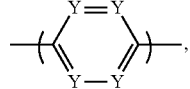
(13)
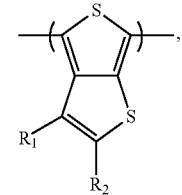
(14)
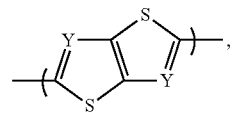
(15)
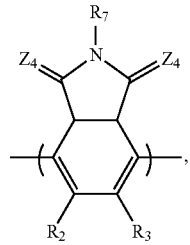
(16)

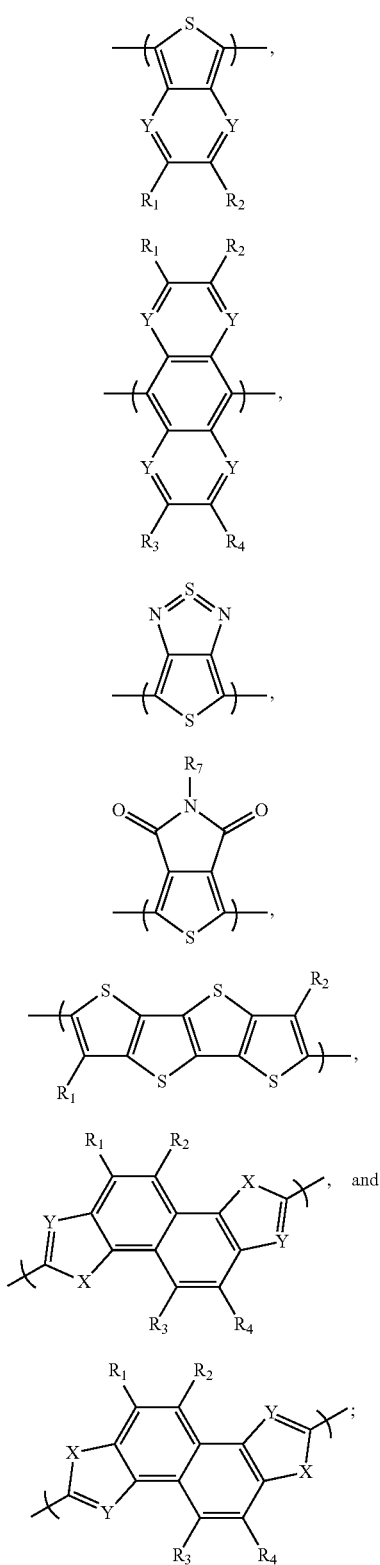

in which each X, independently, is O, S, or Se; each Y, independently, is N or C($R_a$); $Z_1$ is N($R_a$), S, Si($R_aR_b$), or C($R_aR_b$); $Z_2$ is O, S, Se, N($R_a$), Si($R_aR_b$), or C($R_aR_b$); $Z_3$ is O, S, or N($R_a$); each $Z_4$, independently, is $CH_2$, O, or S; each of $R_1$, $R_2$, $R_3$, $R_4$, $R_5$, and $R_6$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$; $R_7$ is H, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $COR_c$, or $COOR_c$; each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl; each $R_b$, independently, is H, halo, $C_1$-$C_{24}$ alkyl, aryl, heteroaryl, $C_3$-$C_{24}$ cycloalkyl, or $C_3$-$C_{24}$ heterocycloalkyl; and each $R_c$, independently, is H, $C_1$-$C_{24}$ alkyl, aryl, heteroaryl, $C_3$-$C_{24}$ cycloalkyl, or $C_3$-$C_{24}$ heterocycloalkyl.

In some embodiments, the moieties of formulas (2)-(23) can be one of the following monomer repeat units: a benzodithiophene moiety, a cyclopentadithiazole moiety, a benzothiadiazole moiety, a thiadiazoloquinoxaline moiety, a benzoisothiazole moiety, a benzothiazole moiety, a dithienopyrrole moiety, a dibenzosilole moiety, a thienothiophene moiety, a carbazole moiety, a dithienothiophene moiety, a tetrahydroisoindole moiety, a fluorene moiety, a silole moiety, a cyclopentadithiophene moiety, a thiazole moiety, a selenophene moiety, a thiazolothiazole moiety, a naphthothiadiazole moiety, a thienopyrazine moiety, a silacyclopentadithiophene moiety, a thiophene moiety, an oxazole moiety, an imidazole moiety, a pyrimidine moiety, a benzoxazole moiety, a benzimidazole moiety, a quinoxaline moiety, a pyridopyrazine moiety, a pyrazinopyridazine moiety, a pyrazinoquinoxaline moiety, a thiadiazolopyridine moiety, a thiadiazolopyridazine moiety, a benzooxadiazole moiety, an oxadiazolopyridine moiety, an oxadiazolopyridazine moiety, a benzoselenadiazole moiety, a benzobisoxazole moiety, a thienothiadiazole moiety, a thienopyrroledione moiety, or a tetrazine moiety.

For example, the moieties of formulas (2)-(23) can be one of the following monomer repeat units: a benzodithiophene moiety of formula (24), a benzodithiophene moiety of formula (25), a cyclopentadithiazole moiety of formula (26), a benzothiadiazole moiety of formula (27), a thiadiazoloquinoxaline moiety of formula (28), a benzoisothiazole moiety of formula (29), a benzothiazole moiety of formula (30), a dithienopyrrole moiety of formula (31), a dibenzosilole moiety of formula (32), a thienothiophene moiety of formula (33), a carbazole moiety of formula (34), a dithienothiophene moiety of formula (35), a fluorene moiety of formula (36), a silole moiety of formula (37), a cyclopentadithiophene moiety of formula (38), a thiazole moiety of formula (39), a selenophene moiety of formula (40), a thiazolothiazole moiety of formula (41), a naphthothiadiazole moiety of formula (42), a thienopyrazine moiety of formula (43), a silacyclopentadithiophene moiety of formula (44), a thiophene moiety of formula (45), an oxazole moiety of formula (46), an imidazole moiety of formula (47), a pyrimidine moiety of formula (48), a benzoxazole moiety of formula (49), a benzimidazole moiety of formula (50), a quinoxaline moiety of formula (51), a pyridopyrazine moiety of formula (52), a pyrazinopyridazine moiety of formula (53), a pyrazinoquinoxaline moiety of formula (54), a thiadiazolopyridine moiety of formula (55), a thiadiazolopyridazine moiety of formula (56), a benzooxadiazole moiety of formula (57), an oxadiazolopyridine moiety of formula (58), an oxadiazolopyridazine moiety of formula (59), a benzoselenadiazole moiety of formula (60), a benzobisoxazole moiety of formula (61), a benzobisoxazole moiety of formula (62), a tetrazine moiety of formula (63), or a tetrafluorobenzene moiety of formula (64):

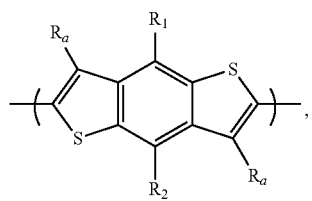 (24)
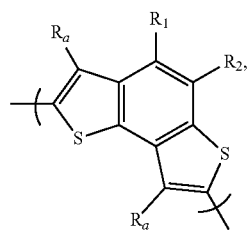 (25)
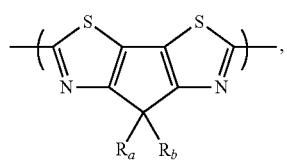 (26)
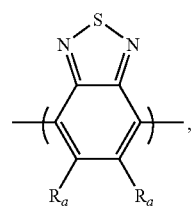 (27)
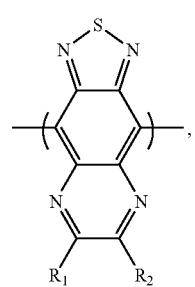 (28)
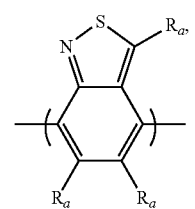 (29)
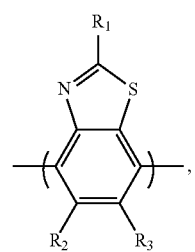 (30)
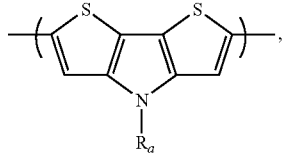 (31)
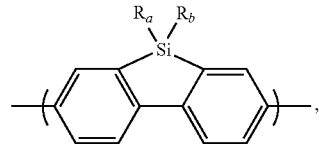 (32)
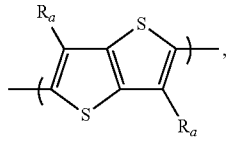 (33)
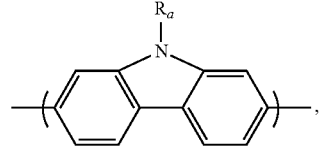 (34)
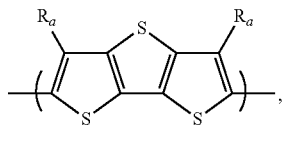 (35)
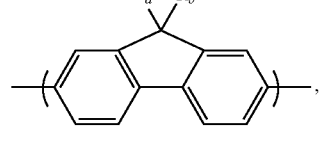 (36)
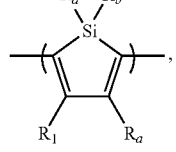 (37)
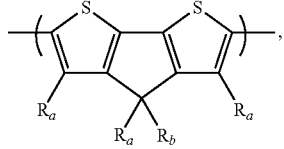 (38)
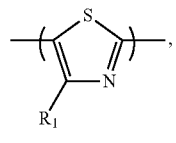 (39)
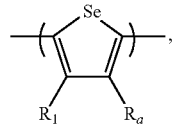 (40)

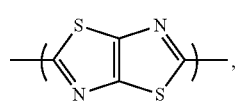 (41)
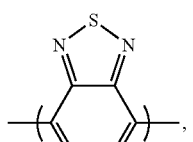 (42)
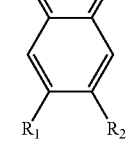 (43)
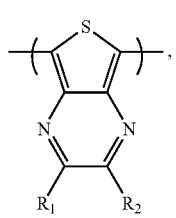 (44)
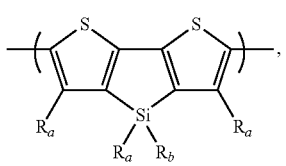 (45)
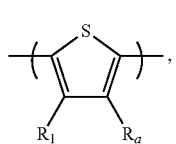 (46)
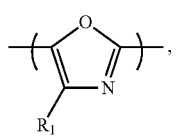 (47)
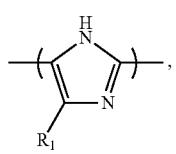 (48)
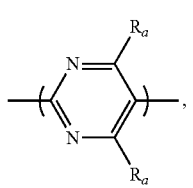 (49)
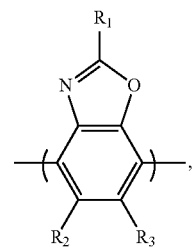 (49)
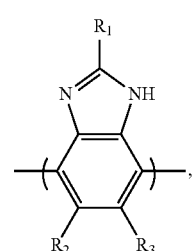 (50)
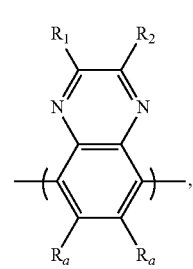 (51)
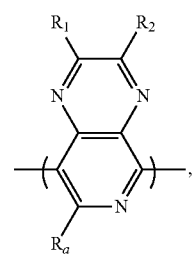 (52)
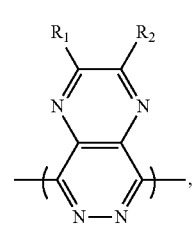 (53)
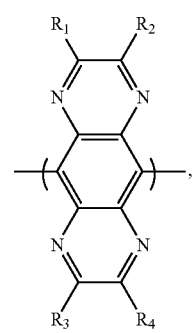 (54)

-continued

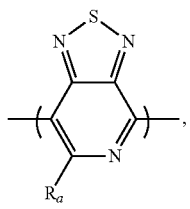
(55)

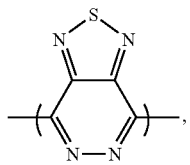
(56)

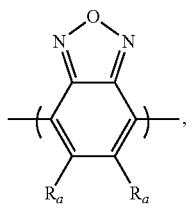
(57)

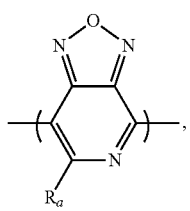
(58)

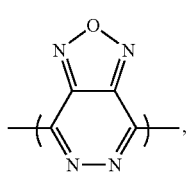
(59)

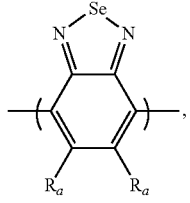
(60)

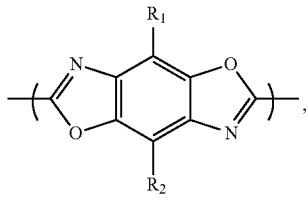
(61)

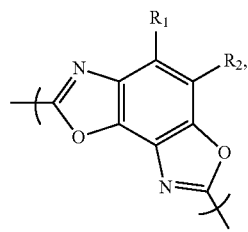
(62)

-continued

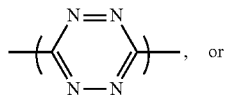
(63)

, or

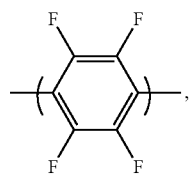
(64)

in which $R_1$, $R_2$, $R_3$, $R_4$, $R_a$, and $R_b$ are defined above.

In some embodiments, the second monomer repeat unit can be a moiety of formula (2), in which each X is S, each Y is $C(R_a)$, and each of $R_1$ and $R_2$, independently, is $OR_c$ or $COOR_c$. In such embodiments, each $R_a$ can be H and each $R_c$ can be $C_1$-$C_{24}$ alkyl.

In some embodiments, the second monomer repeat unit can be a moiety of formula (6), in which each Y is $C(R_a)$ and $Z_1$ is $Si(R_aR_b)$. In such embodiments, each $R_a$, independently, can be H or $C_1$-$C_{24}$ alkyl, and $R_b$ can be $C_1$-$C_{24}$ alkyl.

In some embodiments, the second monomer repeat unit can be a moiety of formula (8), in which Y is $C(R_a)$ and $Z_2$ is S. In such embodiments, $R_1$ in formula (8) can be $C_1$-$C_{24}$ alkyl and $R_a$ can be $C_1$-$C_{24}$ alkyl.

In some embodiments, the photoactive polymer described herein can further include an optional third monomer repeat unit different from the first and second monomer repeat units. The third monomer repeat unit can be either an electron donating moiety or an electron accepting moiety. In some embodiments, the third monomer repeat unit can be a moiety selected from the group consisting of the moieties of formulas (2)-(23) described above (e.g., the moieties of formulas (24)-(64))

As an example, the third monomer repeat unit can be a moiety of formula (8):

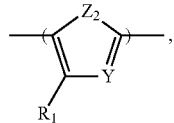
(8)

in which Y is N or $C(R_a)$; $Z_2$ is O, S, Se, $N(R_a)$, $Si(R_aR_b)$, or $C(R_aR_b)$; $R_1$ is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$; each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl; $R_b$ is H, halo, $C_1$-$C_{24}$ alkyl, aryl, heteroaryl, $C_3$-$C_{24}$ cycloalkyl, or $C_3$-$C_{24}$ heterocycloalkyl; and $R_c$ is H, $C_1$-$C_{24}$ alkyl, aryl, heteroaryl, $C_3$-$C_{24}$ cycloalkyl, or $C_3$-$C_{24}$ heterocycloalkyl. In this example, $R_1$ can be H, Y can be $C(R_a)$ (in which $R_a$ can be H), and $Z_2$ can be S.

In some embodiments, the photoactive polymer described herein can further include an optional fourth monomer repeat unit different from the first, second, and third monomer repeat units. The fourth monomer repeat unit can be either an electron donating moiety or an electron accepting moiety. In some embodiments, the fourth monomer repeat unit can be a moiety selected from the group consisting of the moieties of formulas (2)-(23) described above (e.g., the moieties of formulas (24)-(64))

As an example, the fourth monomer repeat unit can be a moiety of formula (13):

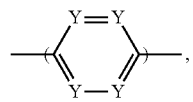
(13)

in which each Y, independently, is N or $C(R_a)$, each $R_a$, independently, being H, halo, $C_1$-$C_{24}$ alkyl, aryl, heteroaryl, $C_3$-$C_{24}$ cycloalkyl, or $C_3$-$C_{24}$ heterocycloalkyl. In this example, each Y can be $C(R_a)$ in which each $R_a$ can be F.

In some embodiments, at least one (e.g., one, two, or three) of the first, second, third, and fourth monomer repeat units is an electron donating moiety. In some embodiments, at least one (e.g., one, two, or three) of the first, second, third, and fourth monomer repeat units is an electron accepting moiety.

In some embodiments, the first, second, third, or fourth monomer repeat unit can be substituted with a group containing a long alkyl chain (e.g., $C_6$-$C_{24}$ alkyl). Without wishing to be bound by theory, it is believed that a monomer repeat unit containing a substituent with a long alkyl chain can result in a polymer with a high solubility in a solvent (e.g., an organic solvent). As a result, such a polymer can have an improved processability and therefore can be used readily to prepare a photoactive layer.

In general, the molar ratio of the first, second, and optional third and fourth monomer repeat units in a photoactive polymer described herein can vary as desired. In some embodiments, the molar ratio of any two of four monomer repeat units can be at least about 1:1 (e.g., at least about 2:1, at least about 3:1, or at least about 4:1) and/or at most about 10:1 (e.g., at most about 5:1, at most about 4:1, at most about 3:1, or at most about 2:1). For example, a photoactive polymer containing three different monomer repeat units can have the first, second, and third monomer repeat units in a molar ratio of about 1:1:2. As another example, a photoactive polymer containing four different monomer repeat units can have the first, second, third, and fourth monomer repeat units in a molar ratio of about 1:2:2:1.

In some embodiments, the photoactive polymer described herein can contain three different monomer repeat units, in which the first monomer repeat unit is a moiety of formula (1), and each of the second and third monomer repeat units is any of the moieties of formulas (2)-(23) (e.g., e.g., the moieties of formulas (24)-(64)). In such embodiments, the photoactive polymer can contain any of 1-100 of the first, second, and third monomer repeat units. Examples of such polymers include the polymers of formula (65)-(67):

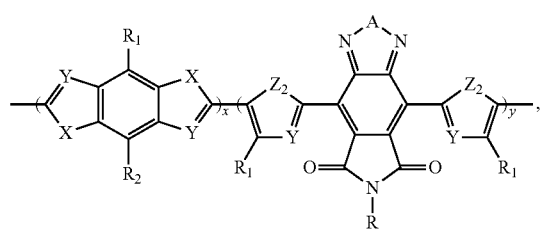
(65)

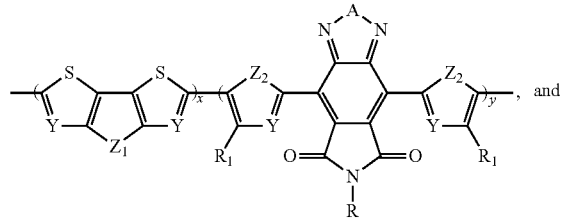
(66)

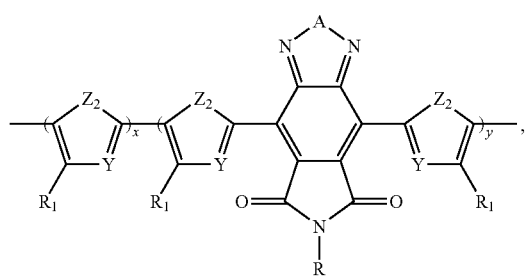
(67)

in which A, X, Y, $Z_1$, $Z_2$, R, $R_1$, and $R_2$ are defined above and each of x and y, independently, can be any integer ranging from 1-200. In some embodiments, x is the same as y.

In some embodiments of formula (65), A can be S; each X can be S; each Y can be $C(R_a)$; each $Z_2$ can be S; R can be $C_1$-$C_{24}$ alkyl optionally containing oxygen and optionally substituted with halo or $C_1$-$C_{24}$ alkoxy; each $R_1$, independently, can be H, $C_1$-$C_{24}$ alkyl, $OR_c$, or $COOR_c$; $R_2$ can be H, $C_1$-$C_{24}$ alkyl, $OR_c$, or $COOR_c$; each $R_a$, independently, can be H or $C_1$-$C_{24}$ alkyl; and each $R_c$, independently, can be H or $C_1$-$C_{24}$ alkyl. In such embodiments, R can be $C_1$-$C_{24}$ alkyl (e.g., $C_{12}H_{25}$ or $C_{20}H_{41}$); each $R_1$ in the thiophene moiety can be H; $R_1$ in the benzodithiophene moiety can be $OR_c$ or $COOR_c$; $R_2$ can be $OR_c$ or $COOR_c$; each $R_a$ can be H; and each $R_c$, independently, can be $C_1$-$C_{24}$ alkyl (e.g., $C_8H_{17}$ or $C_{12}H_{25}$). In such embodiments, the pyrrolo[3,4-f]-2,1,3-benzothiadiazole-5,7-dione moiety is the first monomer repeat unit, the benzodithiophene moiety can be the second monomer repeat unit, and the two thiophene moieties can be the third monomer repeat unit. Exemplary polymers of formula (65) include

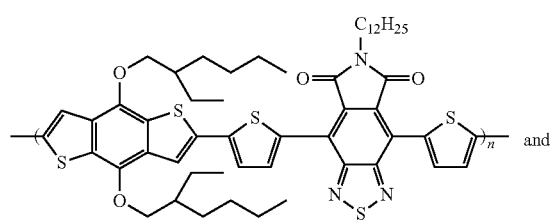
(polymer 1)

and

-continued

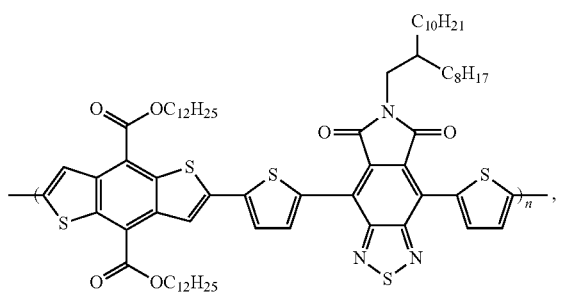

(polymer 2)

in which n can be any integer ranging from 1-200.

In some embodiments of formula (66), A can be S; each Y can be $C(R_a)$; $Z_1$ can be $Si(R_aR_b)$; each $Z_2$ can be S; R can be $C_1$-$C_{24}$ alkyl optionally containing oxygen and optionally substituted with halo or $C_1$-$C_{24}$ alkoxy; each $R_1$, independently, can be H or $C_1$-$C_{24}$ alkyl; each $R_a$, independently, can be H or $C_1$-$C_{24}$ alkyl; and $R_b$ can be H or $C_1$-$C_{24}$ alkyl. In such embodiments, R can be $C_1$-$C_{24}$ alkyl (e.g., $C_{12}H_{25}$ or $C_{20}H_{41}$); each $R_1$ can be H; each $R_a$ in the thiophene moiety can be H; $R_a$ in the silacyclopentadithiophene moiety can be $C_1$-$C_{24}$ alkyl (e.g., $C_8H_{17}$); and $R_b$ can be $C_1$-$C_{24}$ alkyl (e.g., $C_8H_{17}$). In such embodiments, the pyrrolo[3,4-f]-2,1,3-benzothiadiazole-5,7-dione moiety is the first monomer repeat unit, the silacyclopentadithiophene moiety can be the second monomer repeat unit, and the two thiophene moieties can be the third monomer repeat unit. An exemplary polymer of formula (66) is

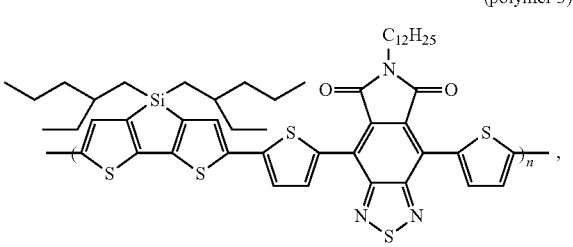

(polymer 3)

in which n can be any integer ranging from 1-200.

In some embodiments of formula (67), A can be S; each Y can be $C(R_a)$; each $Z_2$ can be S; R can be $C_1$-$C_{24}$ alkyl optionally containing oxygen and optionally substituted with halo or $C_1$-$C_{24}$ alkoxy; each $R_1$, independently, can be H or $C_1$-$C_{24}$ alkyl; and each $R_a$, independently, can be H or $C_1$-$C_{24}$ alkyl. In such embodiments, R can be $C_1$-$C_{24}$ alkyl (e.g., $C_{12}H_{25}$ or $C_{20}H_{41}$); $R_1$ in the thiophene moiety having x units can be $C_1$-$C_{24}$ alkyl (e.g., $C_{12}H_{25}$ or $C_{20}H_{41}$); each $R_1$ in the thiophene moieties bonded to the pyrrolo[3,4-f]-2,1,3-benzothiadiazole-5,7-dione moiety can be H; each $R_a$ can be H. In such embodiments, the pyrrolo[3,4-f]-2,1,3-benzothiadiazole-5,7-dione moiety is the first monomer repeat unit, the thiophene moiety having x units can be the second monomer repeat unit, and the two thiophene moieties bonded to the first, monomer repeat unit can be the third monomer repeat unit. An exemplary polymer of formula (67) is

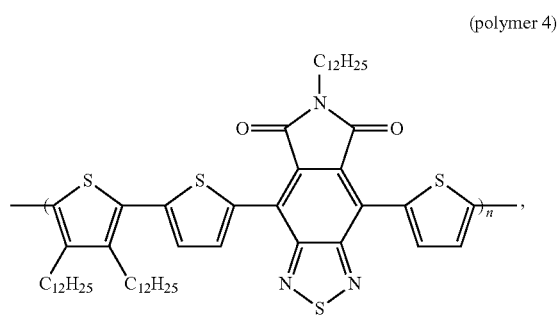

(polymer 4)

in which n can be any integer ranging from 1-200.

In some embodiments, the photoactive polymer described herein can contain four different monomer repeat units, in which the first monomer repeat unit is a moiety of formula (1), and each of the second, third, and fourth monomer repeat units is any of the moieties of formulas (2)-(23) (e.g., e.g., the moieties of formulas (24)-(64)). In such embodiments, the photoactive polymer can contain any of 1-100 of the first, second, third, and fourth monomer repeat units. Examples of such polymers include the polymers of formula (68):

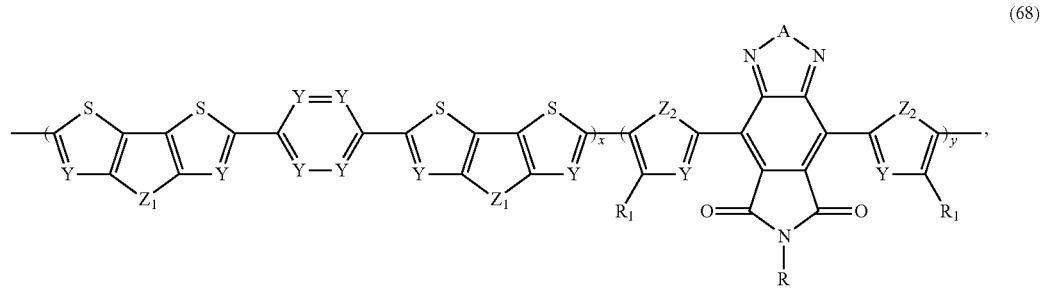

(68)

in which A, Y, $Z_1$, $Z_2$, R, and $R_1$ are defined above and each of x and y, independently, can be any integer ranging from 1-200. In some embodiments, x is the same as y.

In some embodiments of formula (68), A can be S; each Y can be $C(R_a)$; each $Z_1$ can be Si; each $Z_2$ can be S; R can be $C_1$-$C_{24}$ alkyl optionally containing oxygen and optionally substituted with halo or $C_1$-$C_{24}$ alkoxy; each $R_1$, independently, can be H or $C_1$-$C_{24}$ alkyl; and each $R_a$, independently, can be H, halo, or $C_1$-$C_{24}$ alkyl. In such embodiments, R can be $C_1$-$C_{24}$ alkyl (e.g., $C_8H_{17}$, $C_{12}H_{25}$, or $C_{20}H_{41}$); each $R_1$ can be H; each $R_a$ in the thiophene and silacyclopentadithiophene moieties can be H; and each $R_a$ in the benzene moiety can be F. In such embodiments, the pyrrolo[3,4-f]-2,1,3-benzothiadiazole-5,7-dione moiety is the first monomer repeat unit, the two silacyclopentadithiophene moieties can be the second monomer repeat unit, the two thiophene moieties can be the third monomer repeat unit, and the benzene moiety can be the fourth monomer repeat unit. Exemplary polymers of formula (68) include In some embodiments, at least one (e.g., one, two, or three) of the first, second, third, and fourth monomer repeat units is an electron donating moiety (e.g., a moiety of formulas (1)-(8), (12)-(15), and (21)-(23)) and at least one (e.g., one, two, or three) of the first, second, third, and fourth monomer repeat units is an electron accepting moiety (e.g., a moiety of formulas (9)-(11) and (16)-(20)).

In some embodiments, the photoactive polymer described herein can contain five or six different monomer repeat units, in which the first monomer repeat unit is a moiety of formula (1), and each of the second, third, fourth, fifth, and sixth monomer repeat units is any of the moieties of formulas (2)-(23) (e.g., e.g., the moieties of formulas (24)-(64)). In such embodiments, the photoactive polymer can contain any of 1-100 of the first, second, third, fourth, fifth, and sixth monomer repeat units. For example, such a photoactive polymer can be a copolymer containing two or more of the polymers of formulas (65)-(68). An example of a photoactive polymer containing six different monomer repeat units is (polymer 5)

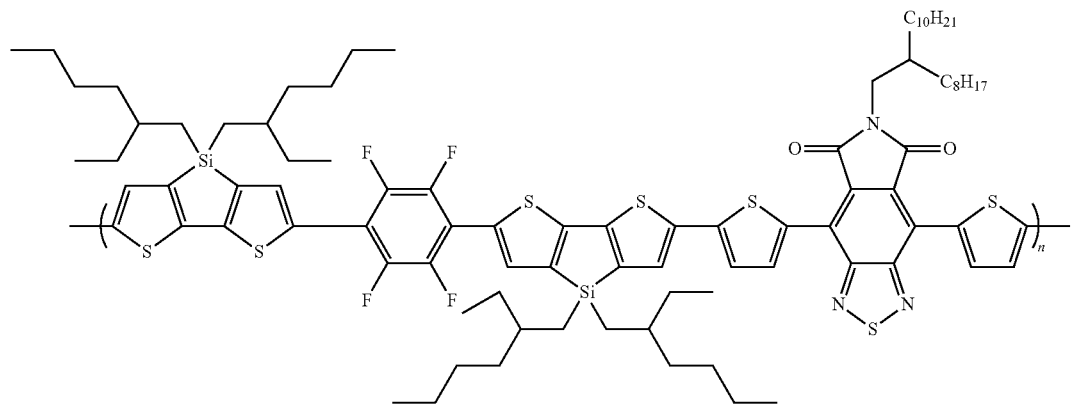

and (polymer 6)

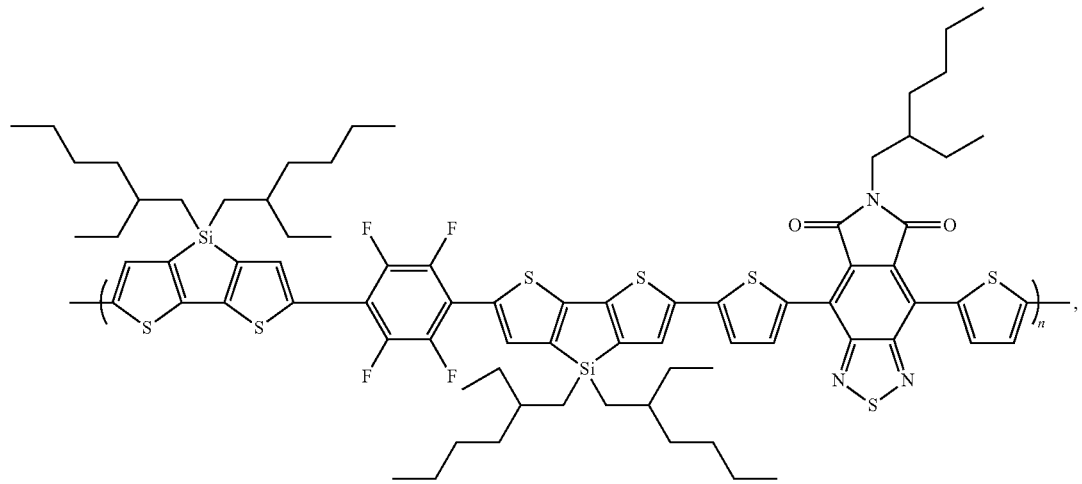

in which n can be any integer ranging from 1-200.

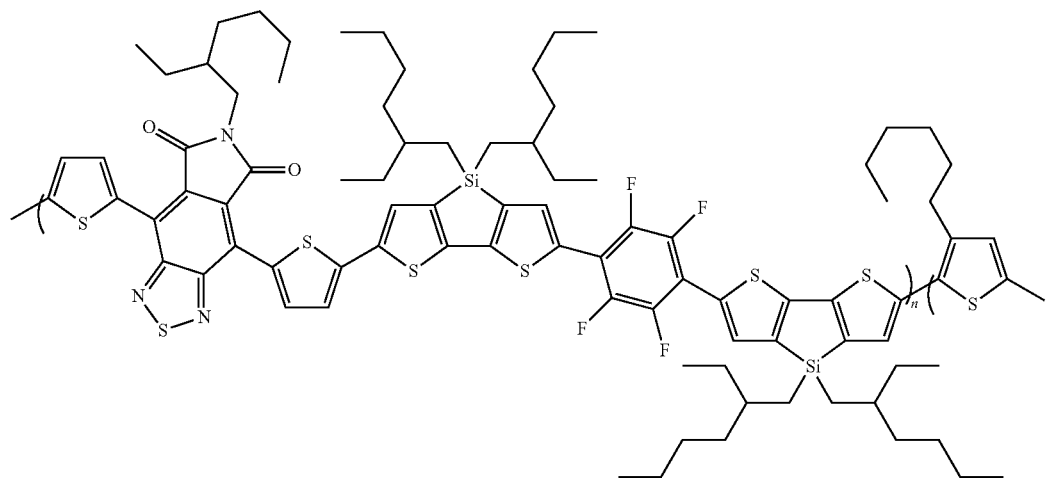

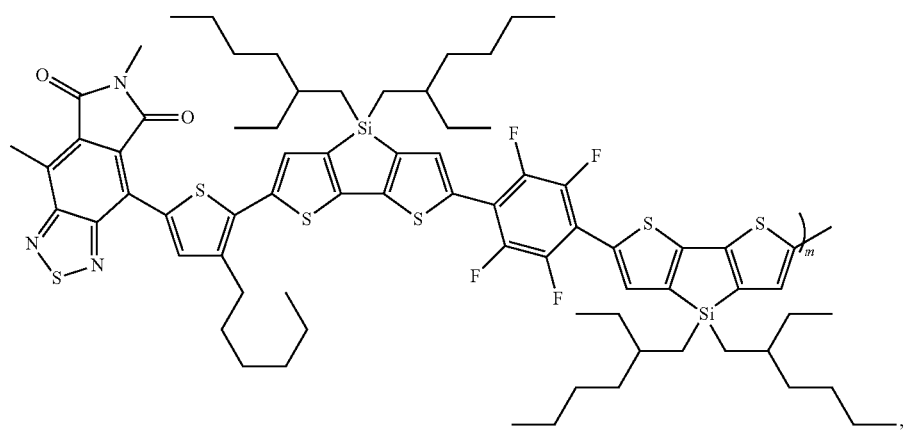

in which n and m can any integer ranging from 1-200.

Without wishing to be bound by theory, it is believed that a photovoltaic cell having a photoactive polymer described herein (e.g., a polymer containing the first, second, and optional third and fourth monomer repeat units described above) can have a relatively high energy conversion efficiency. In some embodiments, such a photovoltaic cell can have an efficiency of at least about 3% (e.g., at least about 3.5%, at least about 4%, at least 4.5%, or at least about 5%) under AM 1.5 conditions. Further, without wishing to be bound by theory, it is believed that other advantages of the photoactive polymers described herein include suitable band gap (e.g., 1.3-1.8 eV) that can improve photocurrent and cell voltage, high positive charge mobility (e.g., $10^{-4}$ to $10^{-1}$ cm$^2$/Vs) that can facilitate charge separation in photoactive layer 140, and high solubility in an organic solvent that can improve film forming ability and processability. In some embodiments, the polymers can be optically non-scattering.

The photoactive polymers described herein can be prepared by methods known in the art or methods described herein. For example, a copolymer can be prepared by a cross-coupling reaction between one or more monomers containing two organometallic groups (e.g., alkylstannyl groups, Grignard groups, or alkylzinc groups) and one or more monomers containing two halo groups (e.g., Cl, Br, or I) in the presence of a transition metal catalyst. As another example, a copolymer can be prepared by a cross-coupling reaction between one or more monomers containing two borate groups and one or more monomers containing two halo groups (e.g., Cl, Br, or I) in the presence of a transition metal catalyst. Other methods that can be used to prepare the copolymers described above including Suzuki coupling reactions, Negishi coupling reactions, Kumada coupling reactions, and Stille coupling reactions, all of which are well known in the art. Examples 1-6 below provide descriptions of how polymers 1-6 listed above were actually prepared.

The monomers can be prepared by the methods described herein or by the methods know in the art, such as those described in U.S. patent application Ser. No. 11/486,536, Coppo et al., *Macromolecules* 2003, 36, 2705-2711, Kurt et al., *J. Heterocycl. Chem.* 1970, 6, 629, Chen et al., *J. Am. Chem. Soc.*, (2006) 128(34), 10992-10993, Hou et al., *Macromolecules* (2004), 37, 6299-6305, and Bijleveld et al., *Adv. Funct. Mater.*, (2009), 19, 3262-3270. The monomers can contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

This disclosure also features the compounds of formula (69):

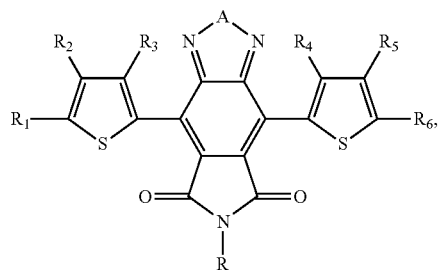

(69)

in which A is O, S, or Se; R is H, $C_1$-$C_{24}$ alkyl optionally containing oxygen, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl; and each of $R_1$, $R_2$, $R_3$, $R_4$, $R_5$, and $R_6$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_C$, $COR_C$, or $COOR_C$, each $R_c$ independently, being H, $C_1$-$C_{24}$ alkyl, aryl, heteroaryl, $C_3$-$C_{24}$ cycloalkyl, or $C_3$-$C_{24}$ heterocycloalkyl. In a subset of the compounds of formula (69), each of $R_1$ and $R_6$ is halo (e.g., F, Cl, Br, or I). In such compounds, A can be S; each of $R_2$, $R_3$, $R_4$, and $R_5$ can be H; and R can be $C_1$-$C_{24}$ alkyl (e.g., $C_8H_{17}$, $C_{12}H_{25}$, or $C_{20}H_{41}$) optionally containing oxygen and optionally substituted with halo or $C_1$-$C_{24}$ alkoxy. The compounds of formula (69) can be used as monomers to prepare the photoactive polymers described herein. Exemplary compounds of formula (69) include compounds 1-3 listed below:

compound 1

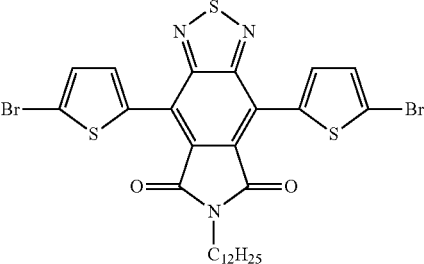

compound 2

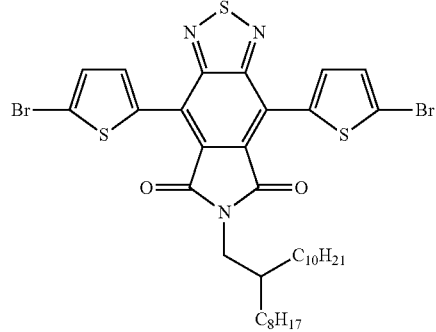

compound 3

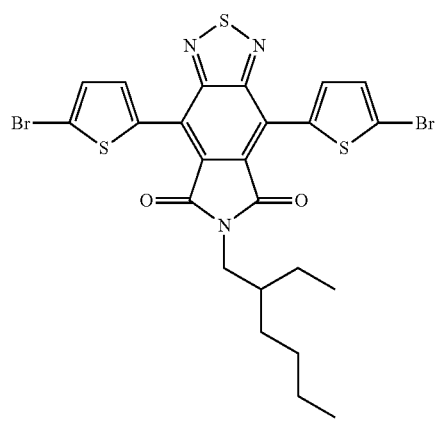

Compounds 1-3 can be prepared by the methods described in Examples 1, 2 and 6 below, respectively.

This disclosure also features the compounds of formula (70):

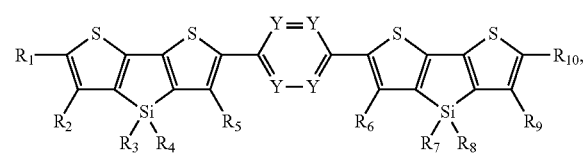

(70)

in which each Y, independently, is N or $C(R_a)$, each $R_a$, independently, being H, halo, $C_1$-$C_{24}$ alkyl, aryl, heteroaryl, $C_3$-$C_{24}$ cycloalkyl, or $C_3$-$C_{24}$ heterocycloalkyl; and each of $R_1$, $R_2$, $R_3$, $R_4$, $R_5$, $R_6$, $R_7$, $R_8$, $R_9$, and $R_{10}$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$, each $R_c$ independently, being H, $C_1$-$C_{24}$ alkyl, aryl, heteroaryl, $C_3$-$C_{24}$ cycloalkyl, or $C_3$-$C_{24}$ heterocycloalkyl. In a subset of the compound of formula (70), each Y can be $C(R_a)$, in which each $R_a$ is halo (e.g., F). In such compounds, each of $R_1$ and $R_{10}$, independently, can be halo (e.g., Br), and each of $R_2$, $R_3$, $R_4$, $R_5$, $R_6$, $R_7$, $R_8$, and $R_9$, independently, can be H or $C_1$-$C_{24}$ alkyl. For example, each of $R_3$, $R_4$, $R_7$, and $R_8$, independently, is $C_1$-$C_{24}$ alkyl (e.g., $C_8H_{17}$) and each of $R_2$, $R_5$, $R_6$, and $R_9$, is H. The compounds of formula (70) can be used as monomers to prepare the photoactive polymers described herein. An exemplary compound of formula (70) is compound 4 listed below:

compound 4

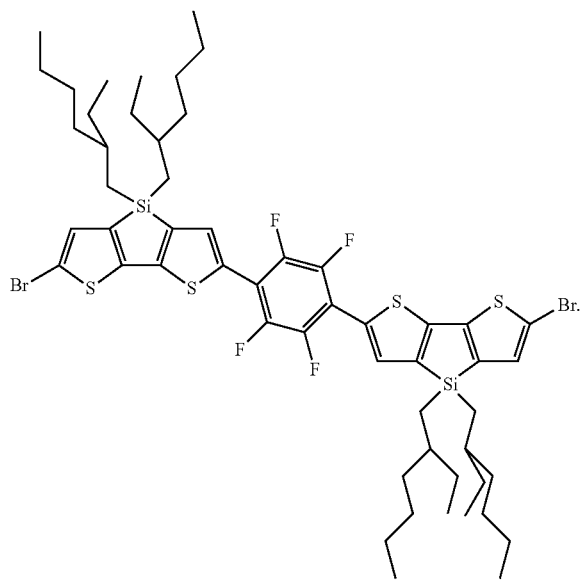

Compound 4 can be prepared by the method described in Example 5 below.

In some embodiments, photoactive layer 140 can include at least one of the photoactive polymer described herein and optionally one or more additional photoactive polymers as the electron donor material. Examples of the additional photoactive polymers include polythiophenes, polyanilines, polycarbazoles, polyvinylcarbazoles, polyphenylenes, polyphenylvinylenes, polysilanes, polythienylenevinylenes, polyisothianaphthanenes, polycyclopentadithiophenes, polysilacyclopentadithiophenes, polycyclopentadithiazoles, polythiazolothiazoles, polythiazoles, polybenzothiadiazoles, poly(thiophene oxide)s, poly(cyclopentadithiophene oxide)s, polythiadiazoloquinoxalines, polybenzoisothiazoles, polybenzothiazoles, polythienothiophenes, poly(thienothiophene oxide)s, polydithienothiophenes, poly(dithienothiopliene oxide)s, polyfluorenes, polytetrahydroisoindoles, and copolymers thereof. In some embodiments, the electron donor material can be polythiophenes (e.g., poly(3-hexylthiophene)), polycyclopentadithiophenes, and copolymers thereof.

Without wishing to be bound by theory, it is believed that incorporating two or more photoactive polymers in photoactive layer 140 can facilitate formation of a photoactive layer with a sufficiently large thickness (e.g., at least about 150 nm, at least about 200 nm, at least about 250 nm, or at least about 300 nm) while still maintaining a sufficiently high fill factor and/or a sufficient light absorbance. A photoactive layer with a relatively large thickness can be readily prepared by using a continuous roll-to-roll process, thereby reducing the manufacturing costs of a photovoltaic cell.

Examples of other photoactive polymers suitable for use in photoactive layer 140 have been described in, e.g., U.S. Pat. Nos. 8,058,550, 7,781,673 and 7,772,485, WO 2011/085004, and U.S. Application Publication Nos. 2010-0224252, 2010-0032018, 2008-0121281, 2008-0087324, and 2007-0020526.

In some embodiments, the electron acceptor material in photoactive layer 140 can include fullerenes. In some embodiments, photoactive layer 140 can include one or more unsubstituted fullerenes and/or one or more substituted fullerenes. Examples of unsubstituted fullerenes include $C_{60}$, $C_{70}$, $C_{76}$, $C_{78}$, $C_{82}$, $C_{84}$, and $C_{92}$. Examples of substituted fullerenes include fullerene substituted with phenyl-butyric acid methyl esters (PCBMs, such as phenyl-C61-butyric acid methyl ester (PCBM-C60) or a phenyl-C71-butyric acid methyl ester (PCBM-C70)) or fullerenes substituted with $C_1$-$C_{20}$ alkoxy optionally further substituted with $C_1$-$C_{20}$ alkoxy and/or halo (e.g., $(OCH_2CH_2)_2OCH_3$ or $OCH_2CF_2OCF_2CF_2OCF_3$). Without wishing to be bound by theory, it is believed that fullerenes substituted with long-chain alkoxy groups (e.g., oligomeric ethylene oxides) or fluorinated alkoxy groups have improved solubility in organic solvents and can form a photoactive layer with improved morphology. Other examples of fullerenes have been described in, e.g., commonly-owned U.S. Pat. No. 7,329,709 and WO 2011/160021. In certain embodiments, a combination of electron acceptor materials (e.g., a substituted fullerene and an unsubstituted fullerene) can be used in photoactive layer 140.

Turning to other components of photovoltaic cell 100, substrate 110 is generally formed of a transparent material. As referred to herein, a transparent material is a material which, at the thickness used in a photovoltaic cell 100, transmits at least about 60% (e.g., at least about 70%, at least about 75%, at least about 80%, at least about 85%) of incident light at a wavelength or a range of wavelengths used during operation of the photovoltaic cell. Exemplary materials from which substrate 110 can be formed include polyethylene terephthalates, polyimides, polyethylene naphthalates, polymeric hydrocarbons, cellulosic polymers, polycarbonates, polyamides, polyethers, and polyether ketones. In certain embodiments, the polymer can be a fluorinated polymer. In some embodiments, combinations of polymeric materials are used. In certain embodiments, different regions of substrate 110 can be formed of different materials.

In general, substrate 110 can be flexible, semi-rigid or rigid (e.g., glass). In some embodiments, substrate 110 has a flexural modulus of less than about 5,000 megaPascals (e.g., less than about 1,000 megaPascals or less than about 500 megaPascals). In certain embodiments, different regions of substrate 110 can be flexible, semi-rigid, or inflexible (e.g., one or more regions flexible and one or more different regions semi-rigid, one or more regions flexible and one or more different regions inflexible).

Typically, substrate 110 is at least about one micron (e.g., at least about five microns or at least about 10 microns) thick and/or at most about 1,000 microns (e.g., at most about 500 microns thick, at most about 300 microns thick, at most about 200 microns thick, at most about 100 microns, or at most about 50 microns) thick.

Generally, substrate 110 can be colored or non-colored. In some embodiments, one or more portions of substrate 110 is/are colored while one or more different portions of substrate 110 is/are non-colored.

Substrate 110 can have one planar surface (e.g., the surface on which light impinges), two planar surfaces (e.g., the surface on which light impinges and the opposite surface), or no planar surfaces. A non-planar surface of substrate 110 can, for example, be curved or stepped. In some embodiments, a non-planar surface of substrate 110 is patterned (e.g., having patterned steps to form a Fresnel lens, a lenticular lens or a lenticular prism).

Electrode 120 is generally formed of an electrically conductive material. Exemplary electrically conductive materials include electrically conductive metals, electrically conductive alloys, electrically conductive polymers, and electrically conductive metal oxides. Exemplary electrically conductive metals include gold, silver, copper, aluminum, nickel, palladium, platinum, and titanium. Exemplary electrically conductive alloys include stainless steel (e.g., 332 stainless steel, 316 stainless steel), alloys of gold, alloys of silver, alloys of copper, alloys of aluminum, alloys of nickel, alloys of palladium, alloys of platinum, and alloys of titanium. Exemplary electrically conducting polymers include polythiophenes (e.g., doped poly(3,4-ethylenedioxythiophene) (doped PEDOT)), polyanilines (e.g., doped polyanilines), polypyrroles (e.g., doped polypyrroles). Exemplary electrically conducting metal oxides include indium tin oxide, fluorinated tin oxide, tin oxide and zinc oxide. In some embodiments, combinations of electrically conductive materials are used.

In some embodiments, electrode 120 can include a mesh electrode. Examples of mesh electrodes are described in co-pending U.S. Patent Application Publication Nos. 20040187911 and 20060090791.

In some embodiments, a combination of the materials described above can be used to form electrode 120.

Optionally, photovoltaic cell 100 can include a hole blocking layer 130. The hole blocking layer is generally formed of a material that, at the thickness used in photovoltaic cell 100, transports electrons to electrode 120 and substantially blocks the transport of holes to electrode 120. Examples of materials from which the hole blocking layer can be formed include LiF, metal oxides (e.g., zinc oxide, titanium oxide), and amines (e.g., primary, secondary, or tertiary amines). Examples of amines suitable for use in a hole blocking layer have been described, for example, in co-pending U.S. Application Publication No. 2008-0264488.

Without wishing to be bound by theory, it is believed that when photovoltaic cell 100 includes a hole blocking layer made of amines, the hole blocking layer can facilitate the formation of ohmic contact between photoactive layer 140 and electrode 120 without being exposed to UV light, thereby reducing damage to photovoltaic cell 100 resulted from UV exposure.

Typically, hole blocking layer 130 is at least about 0.02 micron (e.g., at least about 0.03 micron, at least about 0.04 micron, or at least about 0.05 micron) thick and/or at most about 0.5 micron (e.g., at most about 0.4 micron, at most about 0.3 micron, at most about 0.2 micron, or at most about 0.1 micron) thick.

Hole carrier layer 150 is generally formed of a material that, at the thickness used in photovoltaic cell 100, transports holes to electrode 160 and substantially blocks the transport of electrons to electrode 160. Examples of materials from which layer 150 can be formed include polythiophenes (e.g., PEDOT), polyanilines, polycarbazoles, polyvinylcarbazoles, polyphenylenes, polyphenylvinylenes, polysilanes, polythienylenevinylenes, polyisothianaphthanenes, and copolymers thereof. In some embodiments, hole carrier layer 150 can include a dopant used in combination with one of the just-mentioned material. Examples of dopants include poly(styrene-sulfonate)s, polymeric sulfonic acids, or fluorinated polymers (e.g., fluorinated ion exchange polymers).

In some embodiments, the materials that can be used to form hole carrier layer 150 include metal oxides, such as titanium oxides, zinc oxides, tungsten oxides, molybdenum oxides, copper oxides, strontium copper oxides, or strontium titanium oxides. The metal oxides can be either undoped or doped with a dopant. Examples of dopants for metal oxides include salts or acids of fluoride, chloride, bromide, and iodide.

In some embodiments, the materials that can be used to form hole carrier layer 150 include carbon allotropes (e.g., carbon nanotubes). The carbon allotropes can be embedded in a polymer binder.

In some embodiments, the hole carrier materials can be in the form of nanoparticles. The nanoparticles can have any suitable shape, such as a spherical, cylindrical, or rod-like shape.

In some embodiments, hole carrier layer 150 can include combinations of hole carrier materials described above.

In general, the thickness of hole carrier layer 150 (i.e., the distance between the surface of hole carrier layer 150 in contact with photoactive layer 140 and the surface of electrode 160 in contact with hole carrier layer 150) can be varied as desired. Typically, the thickness of hole carrier layer 150 is at least about 0.01 micron (e.g., at least about 0.05 micron, at least about 0.1 micron, at least about 0.2 micron, at least about 0.3 micron, or at least about 0.5 micron) and/or at most about five microns (e.g., at most about three microns, at most about two microns, or at most about one micron). In some embodiments, the thickness of hole carrier layer 150 is from about 0.01 micron to about 0.5 micron.

Electrode 160 is generally formed of an electrically conductive material, such as one or more of the electrically conductive materials described above with respect to electrode 120. In some embodiments, electrode 160 is formed of a combination of electrically conductive materials. In certain embodiments, electrode 160 can be formed of a mesh electrode. In some embodiments, each of electrodes 120 and 160 can be formed of a mesh electrode described herein.

Substrate 170 can be identical to or different from substrate 110. In some embodiments, substrate 170 can be formed of one or more suitable polymers, such as the polymers used in substrate 110 described above.

Figure 2:
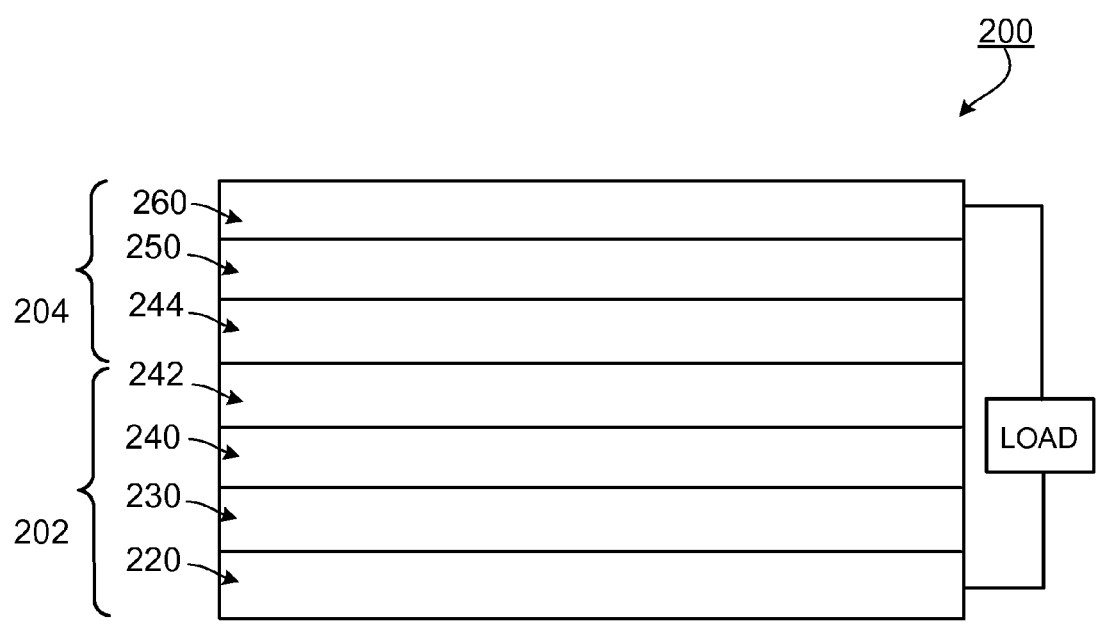
FIG. 2 is a cross-sectional view of an embodiment of a tandem photovoltaic cell.

In some embodiments, the photoactive polymers described herein can be used as an electron donor material in a photoactive layer in a system in which two photovoltaic cells share a common electrode. Such a system is also known as tandem photovoltaic cell. FIG. 2 shows a tandem photovoltaic cell 200 having two semi-cells 202 and 204. Semi-cell 202 includes an electrode 220, an optional hole blocking layer 230, a first photoactive layer 240, and a recombination layer 242. Semi-cell 204 includes recombination layer 242, a second photoactive layer 244, a hole carrier layer 250, and an electrode 260. An external load is connected to photovoltaic cell 200 via electrodes 220 and 260.

Depending on the production process and the desired device architecture, the current flow in a semi-cell can be reversed by changing the electron/hole conductivity of a certain layer (e.g., changing hole blocking layer 230 to a hole carrier layer). By doing so, the semi-cells in a tandem cell can be electrically interconnected either in series or in parallel.

A recombination layer refers to a layer in a tandem cell where the electrons generated from a first semi-cell recombine with the holes generated from a second semi-cell. Recombination layer 242 typically includes a p-type semiconductor Material and an n-type semiconductor material. In general, n-type semiconductor materials selectively transport electrons and p-type semiconductor materials selectively transport holes. As a result, electrons generated from the first semi-cell recombine with holes generated from the second semi-cell at the interface of the n-type and p-type semiconductor materials.

In some embodiments, the p-type semiconductor material includes a polymer and/or a metal oxide. Examples p-type semiconductor polymers include benzodithiophene-containing polymers, polythiophenes (e.g., poly(3,4-ethylene dioxythiophene) (PEDOT)), polyanilines, polyvinylcarbazoles, polyphenylenes, polyphenylvinylenes, polysilanes, polythienylenevinylenes, polyisothianaphthanenes, polycyclopentadithiophenes, polysilacyclopentadithiophenes, polycyclopentadithiazoles, polythiazoles, polybenzothiadiazoles, poly (thiophene oxide)s, poly(cyclopentadithiophene oxide)s, polythiadiazoloquinoxaline, polybenzoisothiazole, polybenzothiazole, polythienothiophene, poly(thienothiophene oxide), polydithienothiophene, poly(dithienothiophene oxide)s, polytetrahydroisoindoles, and copolymers thereof. The metal oxide can be an intrinsic p-type semiconductor (e.g., copper oxides, strontium copper oxides, or strontium titanium oxides) or a metal oxide that forms a p-type semiconductor after doping with a dopant (e.g., p-doped zinc oxides or p-doped titanium oxides). Examples of dopants include salts or acids of fluoride, chloride, bromide, and iodide. In some embodiments, the metal oxide can be used in the form of nanoparticles.

In some embodiments, the n-type semiconductor material (either an intrinsic or doped n-type semiconductor material) includes a metal oxide, such as titanium oxides, zinc oxides, tungsten oxides, molybdenum oxides, and combinations thereof. The metal oxide can be used in the form of nanoparticles. In other embodiments, the n-type semiconductor material includes a material selected from the group consisting of fullerenes (such as those described above), inorganic nanoparticles, oxadiazoles, discotic liquid crystals, carbon nanorods, inorganic nanorods, polymers containing CN groups, polymers containing $CF_3$ groups, and combinations thereof.

In some embodiments, the p-type and n-type semiconductor materials are blended into one layer. In certain embodiments, recombination layer 242 includes two layers, one layer including the p-type semiconductor material and the other layer including the n-type semiconductor material. In such embodiments, recombination layer 242 can further include an electrically conductive layer (e.g., a metal layer or mixed n-type and p-type semiconductor materials) at the interface of the two layers.

In some embodiments, recombination layer 242 includes at least about 30 wt % (e.g., at least about 40 wt % or at least about 50 wt %) and/or at most about 70 wt % (e.g., at most about 60 wt % or at most about 50 wt %) of the p-type semiconductor material. In some embodiments, recombination layer 242 includes at least about 30 wt % (e.g., at least about 40 wt % or at least about 50 wt %) and/or at most about 70 wt % (e.g., at most about 60 wt % or at most about 50 wt %) of the n-type semiconductor material.

Recombination layer 242 generally has a sufficient thickness so that the layers underneath are protected from any solvent applied onto recombination layer 242. In some embodiments, recombination layer 242 can have a thickness of at least about 10 nm (e.g., at least about 20 nm, at least about 50 nm, or at least about 100 nm) and/or at most about 500 nm (e.g., at most about 200 nm, at most about 150 nm, or at most about 100 nm).

In general, recombination layer 242 is substantially transparent. For example, at the thickness used in a tandem photovoltaic cell 200, recombination layer 242 can transmit at least about 70% (e.g., at least about 75%, at least about 80%, at least about 85%, or at least about 90%) of incident light at a wavelength or a range of wavelengths (e.g., from about 350 nm to about 1,000 nm) used during operation of the photovoltaic cell.

Recombination layer 242 generally has a sufficiently low surface resistance. In some embodiments, recombination layer 242 has a surface resistance of at most about $1\times10^6$ ohm/square (e.g., at most about $5\times10^5$ ohm/square, at most about $2\times10^5$ ohm/square, or at most about $1\times10^5$ ohm/square).

Without wishing to be bound by theory, it is believed that recombination layer 242 can be considered as a common electrode between two semi-cells (e.g., one including electrode 220, hole blocking layer 230, photoactive layer 240, and recombination layer 242, and the other include recombination layer 242, photoactive layer 244, hole carrier layer 250, and electrode 260) in photovoltaic cell 200. In some embodiments, recombination layer 242 can include an electrically conductive grid (e.g., mesh) material, such as those described above. An electrically conductive grid material can provide a selective contact of the same polarity (either p-type or n-type) to the semi-cells and provide a highly conductive but transparent layer to transport electrons to a load.

In some embodiments, a one-layer recombination layer 242 can be prepared by applying a blend of an n-type semiconductor material and a p-type semiconductor material on a photoactive layer. For example, an n-type semiconductor and a p-type semiconductor can be first dispersed and/or dissolved in a solvent together to form a dispersion or solution, which can then be coated on a photoactive layer to form a recombination layer.

In some embodiments, a two-layer recombination layer can be prepared by applying a layer of an n-type semiconductor material and a layer of a p-type semiconductor material separately. For example, when titanium oxide nanoparticles are used as an n-type semiconductor material, a layer of titanium oxide nanoparticles can be formed by (1) dispersing a precursor (e.g., a titanium salt) in a solvent (e.g., an anhydrous alcohol) to form a dispersion, (2) coating the dispersion on a photoactive layer, (3) hydrolyzing the dispersion to form a titanium oxide layer, and (4) drying the titanium oxide layer. As another example, when a polymer (e.g., PEDOT) is used as a p-type semiconductor, a polymer layer can be formed by first dissolving the polymer in a solvent (e.g., an anhydrous alcohol) to form a solution and then coating the solution on a photoactive layer.

Other components in tandem cell 200 can be formed of the same materials, or have the same characteristics, as those in photovoltaic cell 100 described above.

Other examples of tandem photovoltaic cells have been described in, e.g., commonly-owned co-pending. U.S. Application Publication Nos. 2007-0272296, 2007-0181179, and 2007-0246094.

In some embodiments, the semi-cells in a tandem cell are electrically interconnected in series. When connected in series, in general, the layers can be in the order shown in FIG. 2. In certain embodiments, the semi-cells in a tandem cell are electrically interconnected in parallel. When interconnected in parallel, a tandem cell having two semi-cells can include the following layers: a first electrode, a first hole blocking layer, a first photoactive layer, a first hole carrier layer (which can serve as an electrode), a second hole carrier layer (which can serve as an electrode), a second photoactive layer, a second hole blocking layer, and a second electrode. In such embodiments, the first and second hole carrier layers can be either two separate layers or can be one single layer. In case the conductivity of the first and second hole carrier layers is not sufficient, an additional layer (e.g., an electrically conductive mesh layer such as a metal mesh layer) providing the required conductivity may be inserted.

In some embodiments, a tandem cell can include more than two semi-cells (e.g., three, four, five, six, seven, eight, nine, ten, or more semi-cells). In certain embodiments, some semi-cells can be electrically interconnected in series and some semi-cells can be electrically interconnected in parallel.

In general, the methods of preparing each layer in photovoltaic cells described in FIGS. 1 and 2 can vary as desired. In some embodiments, a layer (e.g., all layers) can be prepared by a liquid-based coating process. In certain embodiments, a layer can be prepared via a gas phase-based coating process, such as chemical or physical vapor deposition processes.

The term "liquid-based coating process" mentioned herein refers to a process that uses a liquid-based coating composition. Examples of the liquid-based coating composition include solutions, dispersions, or suspensions. The liquid-based coating process can be carried out by using at least one of the following processes: solution coating, ink jet printing, spin coating, dip coating, knife coating, bar coating, spray coating, roller coating, slot coating, gravure coating, flexographic printing, or screen printing. Examples of liquid-based coating processes have been described in, for example, commonly-owned co-pending U.S. Application Publication No. 2008-0006324.

In some embodiments, when a layer includes inorganic semiconductor nanoparticles, the liquid-based coating process can be carried out by (1) mixing the nanoparticles with a solvent (e.g., an aqueous solvent or an anhydrous alcohol) to form a dispersion, (2) coating the dispersion onto a substrate, and (3) drying the coated dispersion. In certain embodiments, a liquid-based coating process for preparing a layer containing inorganic metal oxide nanoparticles can be carried out by (1) dispersing a precursor (e.g., a titanium salt) in a suitable solvent (e.g., an anhydrous alcohol) to form a dispersion, (2) coating the dispersion on a substrate, (3) hydrolyzing the dispersion to form an inorganic semiconductor nanoparticles layer (e.g., a titanium oxide nanoparticles layer), and (4) drying the inorganic semiconductor material layer. In certain embodiments, the liquid-based coating process can be carried out by a sol-gel process (e.g., by forming metal oxide nanoparticles as a sol-gel in a dispersion before coating the dispersion on a substrate).

In general, the liquid-based coating process used to prepare a layer containing an organic semiconductor material can be the same as or different from that used to prepare a layer containing an inorganic semiconductor material. In some embodiments, to prepare a layer that includes an organic semiconductor material, the liquid-based coating process can be carried out by mixing the organic semiconductor material with a solvent (e.g., an organic solvent) to form a solution or a dispersion, coating the solution or dispersion on a substrate, and drying the coated solution or dispersion.

In some embodiments, the photovoltaic cells described in FIGS. 1 and 2 can be prepared in a continuous manufacturing process, such as a roll-to-roll process, thereby significantly reducing the manufacturing cost. Examples of roll-to-roll processes have been described in, for example, commonly-owned co-pending U.S. Pat. No. 7,476,278.

While certain embodiments have been disclosed, other embodiments are also possible.

In some embodiments, photovoltaic cell 100 includes a cathode as a bottom electrode and an anode as a top electrode. In some embodiments, photovoltaic cell 100 can include an anode as a bottom electrode and a cathode as a top electrode.

In some embodiments, photovoltaic cell 100 can include the layers shown in FIG. 1 in a reverse order. In other words, photovoltaic cell 100 can include these layers from the bottom to the top in the following sequence: a substrate 170, an electrode 160, a hole carrier layer 150, a photoactive layer 140, an optional hole blocking layer 130, an electrode 120, and a substrate 110.

In some embodiments, one of substrates 110 and 170 can be transparent. In other embodiments, both of substrates 110 and 170 can be transparent.

Figure 3:
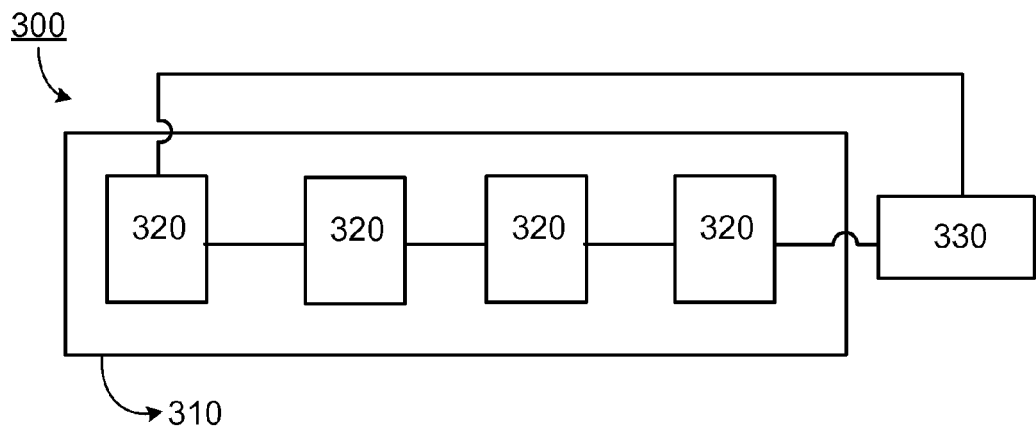
FIG. 3 is a schematic of a system containing multiple photovoltaic cells electrically connected in series.
Figure 4:
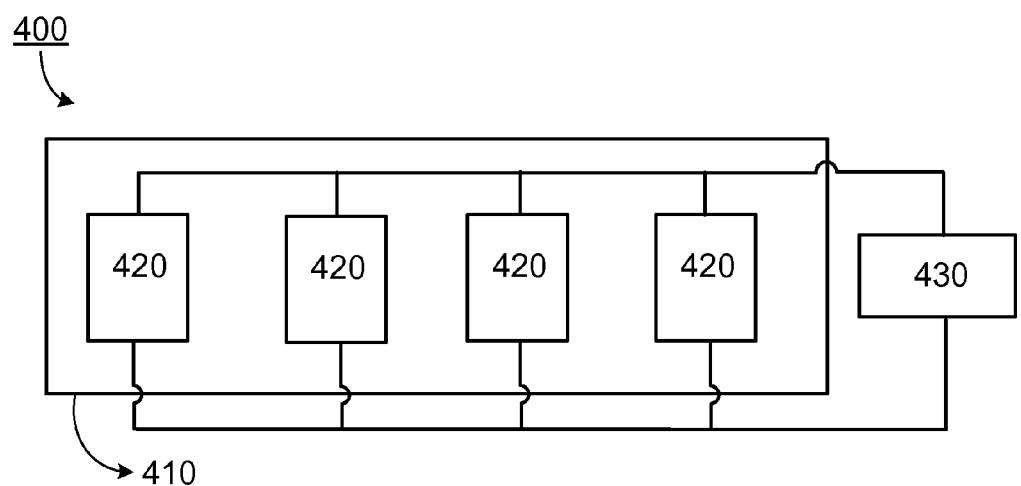
FIG. 4 is a schematic of a system containing multiple photovoltaic cells electrically connected in parallel.

In some embodiments, multiple photovoltaic cells can be electrically connected to form a photovoltaic system. As an example, FIG. 3 is a schematic of a photovoltaic system 300 having a module 310 containing a plurality of photovoltaic cells 320. Cells 320 are electrically connected in series, and system 300 is electrically connected to a load 330. As another example, FIG. 4 is a schematic of a photovoltaic system 400 having a module 410 that contains a plurality of photovoltaic cells 420. Cells 420 are electrically connected in parallel, and system 400 is electrically connected to a load 430. In some embodiments, some (e.g., all) of the photovoltaic cells in a photovoltaic system can be disposed on one or more common substrates. In certain embodiments, some photovoltaic cells in a photovoltaic system are electrically connected in series, and some of the photovoltaic cells in the photovoltaic system are electrically connected in parallel.

While organic photovoltaic cells have been described, other photovoltaic cells can also be integrated with one of the photoactive polymers described herein. Examples of such photovoltaic cells include dye sensitized photovoltaic cells and inorganic photoactive cells with a photoactive material formed of amorphous silicon, cadmium selenide, cadmium telluride, copper indium selenide, and copper indium gallium selenide. In some embodiments, a hybrid photovoltaic cell can be integrated with one of the photoactive polymers described herein.

While photovoltaic cells have been described above, in some embodiments, the photoactive polymers described herein can be used in other devices and systems. For example, the photoactive polymers can be used in suitable organic semiconductive devices, such as field effect transistors, photodetectors (e.g., IR detectors), photovoltaic detectors, imaging devices (e.g., RGB imaging devices for cameras or medical imaging systems), light emitting diodes (LEDs) (e.g., organic LEDs (OLEDs) or IR or near IR LEDs), lasing devices, conversion layers (e.g., layers that convert visible emission into IR emission), amplifiers and emitters for telecommunication (e.g., dopants for fibers), storage elements (e.g., holographic storage elements), and electrochromic devices (e.g., electrochromic displays).

The contents of all publications cited herein (e.g., patents, patent application publications, and articles) are hereby incorporated by reference in their entirety.

The following examples are illustrative and not intended to be limiting.

EXAMPLE 1

Synthesis of Polymer 1

Synthesis of 5,6-Dimethyl ester-4,7-bis(2-bromo-thiophene)-2,1,3-benzothiadiazole

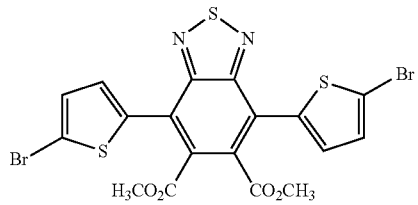 [SMILES: COC(=O)c1c(C(=O)OC)c(-c2ccc(Br)s2)c2nsnc2c1-c1ccc(Br)s1]

To a 100 ml round bottom flask were added 1.03 g (2.22 mmol) of 4,6-bis(5-bromo-2-thienyl)thieno[3,4-c][1,2,5]thiadiazole, 1 mL (~8.1 mmol) of dimethyl acetylenedicarboxylate and 50 mL of toluene. After the mixture was refluxed for 12 hours, the solvent was removed in vacuum. The crude product was purified by column chromatography to provide 605 mg of pure 5,6-dimethyl ester 4,7-bis(2-bromo-thiophene)-2,1,3-benzothiadiazole.

Synthesis of 5,6-Dicarboxylic acid-4,7-bis(2-bromo-thiophene)-2,1,3-benzothiadiazole

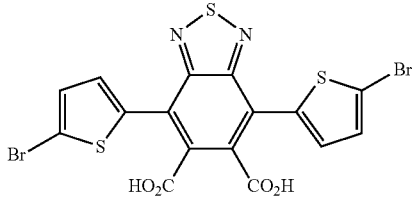 [SMILES: O=C(O)c1c(C(=O)O)c(-c2ccc(Br)s2)c2nsnc2c1-c1ccc(Br)s1]

To a 100 mL round bottom flask were added 600 mg (1.0 mmol) of 5,6-dimethyl ester 4,7-bis(2-bromo-thiophene)-2,1,3-benzothiadiazole, 0.9 g (22.5 mmol) of NaOH, and 25 mL of ethanol. After the reaction mixture was refluxed for 16 hours, the solvent was removed in vacuum. Water was added to the residue and then concentrated HCl was added to the slurry till a pH of 2 was reached. The precipitate from acidification was collected and dried in vacuum to give 540 mg of 5,6-dicarboxylic acid-4,7-bis(2-bromo-thiophene)-2,1,3-benzothiadiazole.

Synthesis of 5,6-Isobenzofuran 1,3-dione-4,7-bis(2-bromo-thiophene)-2,1,3-benzothiadiazole

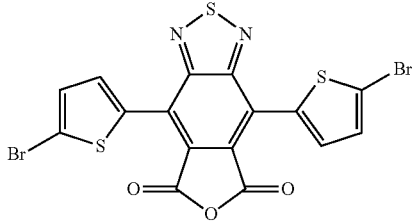 [SMILES: O=C1OC(=O)c2c1c(-c1ccc(Br)s1)c1nsnc1c2-c1ccc(Br)s1]

To a 250 mL round bottom flask were added 540 mg (0.99 mmol) of 5,6-dicarboxylic acid-4,7-bis(2-bromo-thiophene)-2,1,3-benzothiadiazole and 200 mL of acetic anhydride. After the mixture was refluxed for 12 hours, the acetic anhydride was removed in vacuum. The crude product was purified by column chromatography to provide 320 mg of pure 5,6-isobenzofuran 1,3-dione-4,7-bis(2-bromo-thiophene)-2,1,3-benzothiadiazole.

Synthesis of 5-Dodecyl-pyrrolo[3,4-f]-4,7-bis(2-bromo-thiophene)-2,1,3-benzo-thiadiazole-5,7(6H)-dione (Compound 1)

(Compound 1)

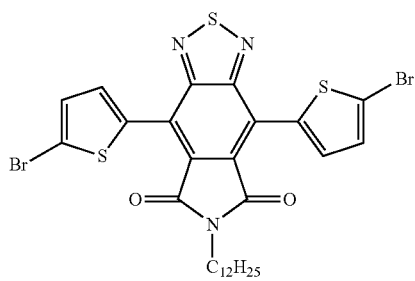

To a 200 mL round bottom flask were added 121 mg (0.22 mmol) of 5,6-isobenzofuran 1,3-dione-4,7-bis(2-bromo-thiophene)-2,1,3-benzothiadiazole, 48 mg (0.25 mmol) of dodecyl amine, and 150 mL of acetic acid. After the mixture was refluxed for 16 hours, acetic acid was removed in vacuum. The crude product was purified by column chromatography to provide 100 mg of Compound 1.

Synthesis of Poly[(4,8-di(2-ethylhexyloxy)benzo[1,2-b;3,4-b]dithiophene)-alt-[5-dodecyl-pyrrolo[3,4-f]-4,7-bis(2-thiophene)-2,1,3-benzothiadiazole-5,7 (6H)-dione (Polymer 1)

(Polymer 1)

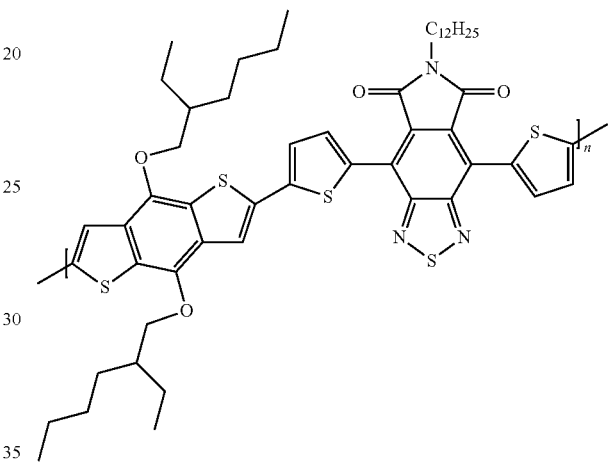

To 100 mL schlenk flask were added 129 mg (0.16 mmol) 2,6-bis(trimethyltin)-4,8-di(2-ethylhexyloxy)benzo[1,2-b;3,4-b]dithiophene (which was prepared following the procedures described in Liang et al., *J. Am. Chem. Soc.* 2009, 131, 7792), 100 mg (0.14 mmol) of Compound 1, 7 mg (11 μmol) of $Pd_2(dba)_3$, 18 mg (59 μmol) of tri-o-tolylphosphine and 20 mL of dry toluene. After the reaction mixture was refluxed for two days, it was cooled to 80° C. An aqueous solution of sodium diethyldithiocarbamate trihydrate (1.5 g in 20 mL water) was introduced into the flask by a syringe. After the mixture was stirred at 80° C. for 12 hours, the mixture was cooled to room temperature and the organic phase was separated from the aqueous layer. The organic layer was then poured into methanol (200 mL). The precipitate was collected and purified by soxhlet extraction to give 30 mg (22%) of polymer 1 with a $M_n$ of about 60,000.

EXAMPLE 2

Synthesis of Polymer 2

Synthesis of 2,6-dibromo didodecyl 4,8-benzodithiophenedicarboxylate 2,6-Dibromo didodecyl 4,8-benzodithiophenedicarboxylate was synthesized based on the Scheme below.

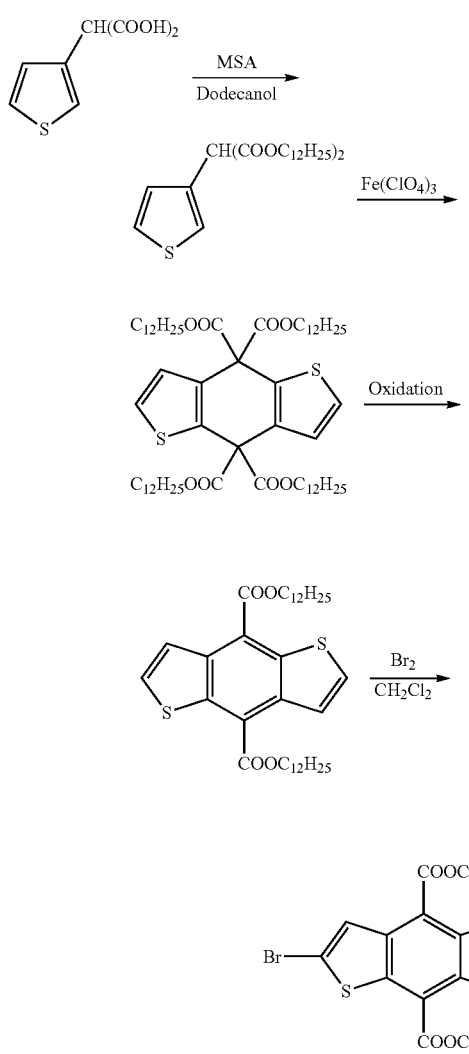

In a one-necked flask, tetradodecyl benzo[1,2-b:4,5-b']dithiophene-4,4,8,8-tetracarboxylate (9.0 g, 8.65 mmol) was dispersed in DMF (80 mL). The mixture was stirred at 120° C. for 10 minutes until the solution became clear. After air was purged in the flask, NaI (800 mg) was added and the reaction mixture was refluxed for 24 hours. After the solvent was evaporated under vacuum, water (30 mL) was added to the residue to form a mixture, which was extracted with $CH_2Cl_2$. The organic layer was combined, dried, and concentrated. The crude product was purified by flash chromatography (eluent: $CH_2Cl_2$:hexane=7:3) to give didodecyl benzo[1,2-b:4,5-b']dithiophene-4,8-dicarboxylate (yield: 1.75 g, 32.9%). $^1$H NMR ($CDCl_3$): 0.9 (6H, t), 1.3 (28H, m), 1.4 (4H, m), 1.6 (4H, m), 1.9 (4H, m), 4.6 (4H, t), 7.8 (2H, d), 8.3 (2H, d).

In a two-necked flask, didodecyl benzo[1,2-b:4,5-b']dithiophene-4,8-dicarboxylate (1.75 g, 2.85 mmol) was dissolved in $CH_2Cl_2$ (100 mL). A solution of $Br_2$ (3 eq., 1.37 g, 8.55 mmol) dissolved in 10 mL $CH_2Cl_2$ was added to the above solution dropwise. After the addition was complete, the reaction mixture was stirred at room temperature overnight. A saturated sodium bisulfite solution was then added to the reaction mixture. After the mixture was extracted with $CH_2Cl_2$, the organic layer was combined, dried, and concentrated. The crude product was purified by flash chromatography (eluent: hexane:$CH_2Cl_2$=3:2) to give 2,6-dibromo didodecyl 4,8-benzo[1,2-b:4,5-b']dithiophenedicarboxylate (yield: 0.93 g, 42.3%). $^1$H NMR ($CDCl^3$): 0.9 (6H, t), 1.3 (28H, m), 1.4 (4H, m), 1.6 (4H, m) 1.9 (4H, m), 4.6 (4H, t), 8.3 (2H, s).

Synthesis of 2,6-Bis(trimethylstannyl)-4,8-benzo[1,2-b:4,5-b']dithiophene-dicarboxylic acid dodecyl ester

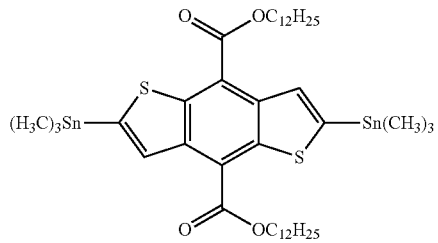

In a one-necked flask, 3-thienylmalonic acid (10.0 g, 53.7 mmol) and 1-dodecanol (4 eq., 40.0 g, 215 mmol) were dissolved in THF (80 mL) at room temperature. To this solution was added methanesulphonic acid (1.99 g, 20.7 mmol). The reaction mixture was stirred at room temperature for 3 days. The solvent was then evaporated at 40° C. The residue was re-dissolved in $CH_2Cl_2$ to form a solution, which was loaded onto a column (eluent: $CH_2Cl_2$) to give didodecyl 2-(thiophen-3-yl)malonate (yield: 18.0 g, 69%). $^1$H NMR ($CDCl_3$): 0.9 (6H, t), 1.3 (36H, m), 1.7 (4H, m), 4.2 (4H, t), 4.8 (1H, s), 7.2 (1H, d), 7.3 (1H, d), 7.4 (1H, s).

In a two-necked flask under argon, a solution of $Fe(ClO_4)_3$ in methanol (320 mL) was prepared at 0° C. A dispersion of didodecyl 2-(thiophen-3-yl)malonate in methanol (120 mL) was added to the solution. After the resulting solution was stirred at 60° C. for 4 hours under argon, the solvent was evaporated under vacuum at room temperature. After water (100 mL) was added to the residue, the aqueous layer was extracted with $CH_2Cl_2$ (100 mL×2) and the organic layer was dried and concentrated. The crude product was purified by flash chromatography (eluent: $CH_2Cl_2$:hexane=3:2) to give tetradodecyl benzo[1,2-b:4,5-b']dithiophene-4,4,8,8-tetracarboxylate (yield: 9.0 g, 50.2%). $^1$H NMR ($CDCl_3$); 0.9 (12H, t), 1.3 (72H, m), 1.7 (8H, m), 4.2 (8H, t), 7.3 (2H, d), 7.4 (2H, d).

To a 200 mL Schlenk flask were added 383 mg (0.496 mmol) of 2,6-dibromo-4,8-benzo[1,2-b:4,5-b']dithiophene-dicarboxylic acid dodecyl ester and 120 mL of dry THF. The solution was cooled to −78° C. A 2.87 M solution of n-BuLi (0.38 mL, 1.1 mmol) was added dropwise to the cooled slurry. After the addition of the nBuLi solution, the reaction mixture was stirred at −78° C. for 30 minutes. A 1.0 M solution of trimethyl tin chloride (1.2 mL, 1.2 mmol) was then added to the reaction mixture. The reaction mixture was allowed to gradually warm to room temperature and stirred overnight. The reaction mixture was poured into a separatory funnel and 200 mL of diethyl ether was added to the funnel. The organic layer was washed 3×100 mL of water and 1×100 mL of brine. After the organic layer was dried with anhydrous $MgSO_4$, the solvent was removed in vacuum. The crude product was purified by column chromatography to provide 103 mg of pure 2,6-bis(trimethylstannyl)-4,8-benzo[1,2-b:4,5-b']dithiophenedicarboxylic acid dodecyl ester.

Synthesis of 5-(2-Octyl-dodecyl)-pyrrolo[3,4-f]-4,7-bis(2-bromo-thiophene)-2,1,3-benzothiadiazole-5,7(6H)-dione (Compound 2)

(Compound 2)

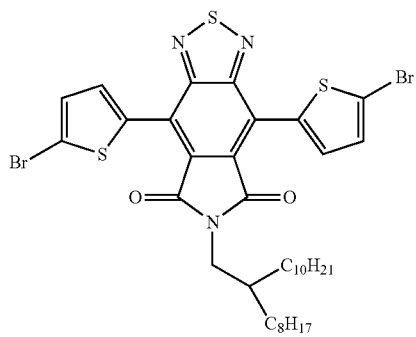

Compound 2 was prepared from the same procedure as Compound 1 described above using appropriate starting materials. 1-Amino-2-octyl-dodecane, one of the starting materials, was prepared by the procedures described in Letizia et al., *J. Am. Chem. Soc.* 2008, 130, 9679.

Synthesis of Poly[(4,8-benzo[1,2-b:4,5-b']dithiophenedicarboxylic acid dodecyl ester)-alt-[5-(2-Octyl-dodecyl)-pyrrolo[3,4-f]-4,7-bis(2-thiophene)-2,1,3-benzothiadiazole-5,7(6H)-dione (Polymer 2)

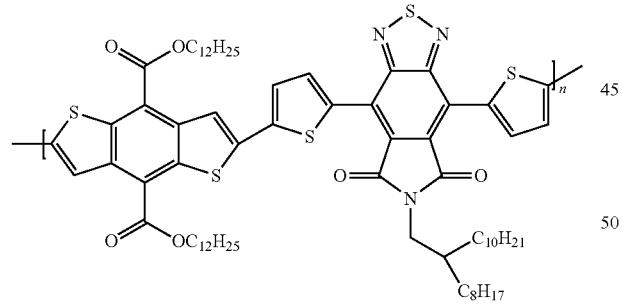

To a 100 mL three neck round bottom flask were added 0.205 g (0.22 mmol) 2,6-bis(trimethylstannyl)-4,8-benzo[1,2-b:4,5-b']dithiophenedicarboxylic acid dodecyl ester, 7 mg (7 mop of Pd$_2$(dba)$_3$, 18 mg (59 μmol) of tri-o-tolylphosphine, 0.159 g (0.197 mmol) of Compound 2 and 20 mL of dry toluene. This reaction mixture was refluxed for two days and then was cooled to 80° C. An aqueous solution of sodium diethyldithio-carbamate trihydrate (1.5 g in 20 mL water) was introduced into the flask by a syringe. The mixture was stirred at 80° C. for 12 hours and then cooled to room temperature. The organic phase was separated from the aqueous layer and poured into methanol (200 mL). The polymer precipitate was collected and then purified by soxhlet extraction to give 28 mg (11%) of Polymer 2 with a M$_n$ of about 17,800.

EXAMPLE 3

Synthesis of Polymer 3

Synthesis of Poly[(4,4-di(2-ethylhexyl)-4H-silolo[3,2-b:4,5-b']dithiophene-2,6-diyl)-alt-[5-dodecyl-pyrrolo[3,4f]-4,7-bis(2-thiophene)-2,1,3-benzothiadiazole-5,7(6H)-dione (Polymer 3)

(Polymer 3)

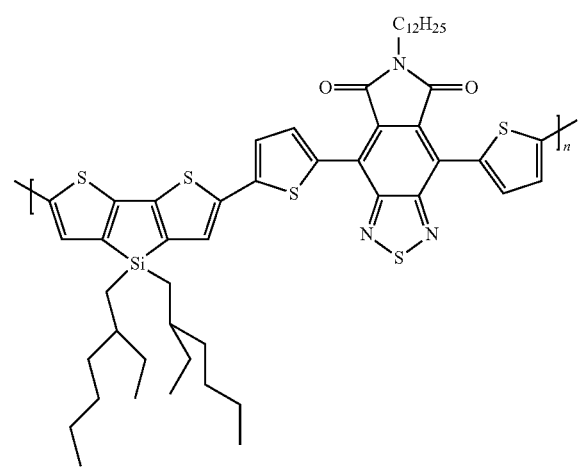

To a 100 mL schlenk flask were added 125 mg (0.17 mmol) of bis(2,6-trimethyl-stannyl)-4,4-di(2-ethylhexyl)-4H-silolo[3,2-b:4,5-b']dithiophene (which was prepared following the procedures described in Hou et al., *J. Am. Chem. Soc.* 2008, 130, 16144), 100 mg (0.14 mmol) of Compound 1 prepared in Example 1, 8 mg (13 mop of Pd$_2$(dba)$_3$, 13 mg (42 μmol) of tri-o-tolylphosphine, and 20 mL of dry toluene. This reaction mixture was refluxed for two days and then cooled to 80° C. An aqueous solution of sodium diethyldithiocarbamate trihydrate (1.5 g in 20 mL water) was introduced into the flask by a syringe. The mixture was stirred at 80° C. for 12 hours and cooled to room temperature. After the organic phase was separated from the aqueous layer, it was poured into methanol (200 mL). The polymer precipitate was collected and purified by soxhlet extraction to give 23 mg (17%) of Polymer 3 with a $M_n$ of about 11,000.

EXAMPLE 4

Synthesis of Polymer 4

Synthesis of 3,4-Didodecyl 2,5 di(trimethyltin)thiophene

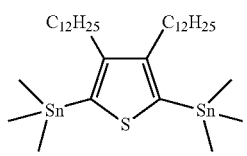

A hot plate with an oil bath and a temperature feedback feature was set to 80° C. 3,4-didodecylthiophene (1 g, 2.377 mmol) (which was prepared following the procedures described in *Macromolecules* 2006, 39, 4289-4297) was added to a dry 500 mL round bottom flask containing a stir bar. A condenser was added and the system was purged with alternating argon. Anhydrous hexane (20 mL), tetramethylethylenediamine (2.125 mL, 14.26 mmol), and n-BuLi in hexane (5.48 mL, 2.6M, 14.26 mmol) were each added in one portion. The flask was dropped into the oil bath at 80° C. and allowed to stir at reflux for ~1.5 hours. The reaction was then cooled to −45° C. in an acetonitrile dry ice bath and allowed to equilibrate for 15 minutes. Trimethyltin chloride in THF (19.01 mL, 1M, 19.01 mmol) was added in one portion. The reaction was observed to turn back to clear colorless upon addition of the tin chloride. The reaction shielded from light. After 15 minutes at −45° C., the reaction was allowed to warm to room temperature and stir overnight. Water was added to quench the reaction and the reaction mixture was extracted 3× with ether. The organic layer was dried over magnesium sulfate, filtered to remove the drying agent, concentrated by rotary evaporation, and purified by chromatography on silica gel using 19:1 hexane:TEA as eluent. After rigorous drying, 1.937 g (>100%) of 3,4-didodecyl 2,5 di(trimethyltin)thiophene having the correct NMR spectrum was obtained as a colorless oil.

Synthesis of Polymer 4

(Polymer 4)

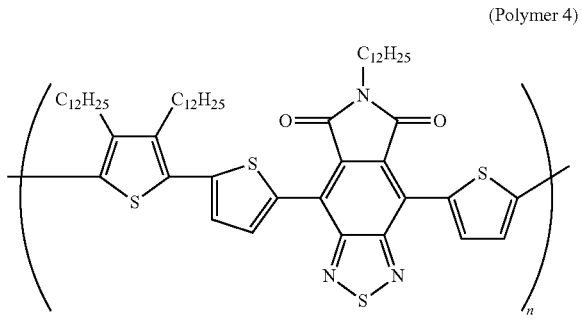

A hot plate with an oil bath and a temperature feedback feature was set to 120° C. and a clean capped condenser was prepared. To a 100 mL round bottom containing a strong stir bar were added 185.9 mg (0.2672 mmol) of Compound 1 prepared from example 1, 219.2 mg (0.2937 mmol, assumed as 95% purity) of 3,4-didodecyl 2,5 di(trimethyltin) thiophene, 6.7 mg (0.007342 mmol) of a palladium catalyst, and 17.9 mg (0.0587 mmol) of a phosphorous ligand. The flask was fitted with the above-mentioned condenser (using a Teflon sleeve) and purged 3× with alternating argon/vacuum cycles. A syringe was used to add anhydrous toluene through the septa on the condenser. The flask was dropped into the oil bath at 120° C. and allowed to stir for 4 days. The reaction was shielded from light. Purple color was observed after 20 minutes. The temperature of the reaction was decreased to 80° C. after 4 days. After 5.29 g (23.49 mmol) of sodium diethyldithiocarbamate trihydrate was added to the reaction mixture in 40 mL of deionized water, the mixture was stirred vigorously for one additional day. The reaction was then removed from heat and the organic phase was allowed to be separated from the aqueous phase. The water layer was removed and the organic phase was washed 2× with deionized water. The organic phase was then poured into 700 mL of methanol to precipitate the polymer. The suspension was filtered to give a crude polymer ($M_n$: 8183, PD: 1.6), which was fractionated in a Soxlet apparatus using methanol (full day), acetone (8 hours), hexane (overnight), DCM (8 hours), chloroform (overnight). The chloroform extract was poured into 700 mL of methanol in order to precipitate the polymer which was filtered to give ~40 mg (yield: 14.2% yield) of Polymer 4 ($M_n$: 16,654, PD: 1.26).

EXAMPLE 5

Synthesis of Polymer 5

Synthesis of 2,3,4,5 tetrafluoro-1,6 bis[6-bromo-4,4-di(2-ethylhexyl)-4H-silolo[3,2-b:4,5-b']dithiophene] benzene

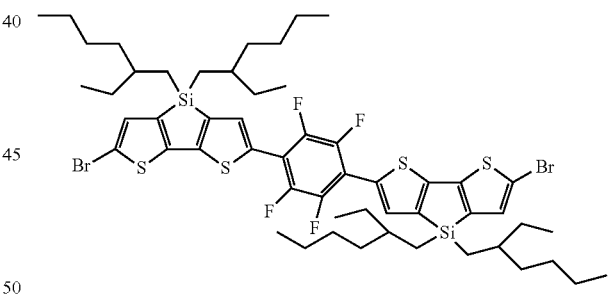

2 g of 4,4-di(2-ethylhexyl)-4H-silolo[3,2-b:4,5-b'] dithiophene (4.776 mmol, 1 eq) prepared in Example 3 was added to 125 ml of dry THF (under Argon). Once a homogenous solution was obtained, the mixture was cooled to −78° C. in a dry ice/acetone bath. The reaction vessel was purged by vacuum and refilled with Argon three times. After the mixture was stirred for 20 minutes at −78° C., 1.5 ml of 2.87 M n-BuLi in hexane (4.298 mmol, 0.9 eq) was added slowly via a syringe. This mixture was stirred for 1.5 hours at −78° C. The reaction vessel, as well as the remaining manipulations, was protected from light. 4.77 ml of 1 M SnMe$_3$Cl in hexane (4.77 mmol, 1 eq) was added to the mixture via a syringe at −78° C. This solution was stirred for 20 minutes at −78° C. and then for 1.5 hours at room temperature. The reaction was then quenched with water and poured into a separatory funnel using ether for the transfer. The mixture was washed with water, poured into a flask, stirred with MgSO$_4$ for 20 minutes at room temperature, filtered and stripped of the solvent. HPLC showed approximately 76% conversion to the mono-tin SiBBt. This mono-tin reaction vessel was flushed with Argon and 0.672 g of 1,4-diiodotetrafluorobenzene (1.672 mmol, 0.35 eq, calculated to ensure the mono-tin was present in excess), 218 mg of tris(dibenzylidene-acetone)-dipalladium (0) (Pd(dBA)$_2$, 5% by mole) and 73 mg of tri-(o-tolyl)phosphine (tri-o-toly, 5% by mole) were added to the flask. The flask was then purged of air by vacuum and flushed with Argon three times. After 100 ml of toluene was then added via a syringe, the reaction was protected from light and heated to 95° C. for 48 hours. The reaction was then cooled to room temperature and quenched with water. The mixture was poured into a separatory funnel, extracted with additional toluene, and washed with water. The organic phase was collected and stripped to dryness. This oil was dissolved in hexane and passed through a short silica plug. All of the product was washed out of the silica plug by using hexane. After the solution was evaporated, the oil was loaded onto a reverse phase silica column. The column was eluted with a gradient of dichloromethane (DCM) in acetonitrile (CAN), beginning with 1 L of 30% DCM in ACN, then 1 L of 35% of DCM in CAN, and finally 2 L of 40% of DCM in ACN. After the product-containing fractions were combined, the solvent was removed by evaporation to give 1.486 g of an intermediate material (yield: ~90%; HPLC purity: ~94%).

After the 1.486 g intermediate material (1.511 mmol, 1 eq) was combined with 0.8066 g of N-bromosuccinimide (NBS, 4.54 mmol, 3 eq), the flask was purged under vacuum and flushed with Argon three times. After 100 ml of chloroform was added via a syringe, the mixture was refluxed overnight (about 16 hours). The reaction was then cooled to room temperature and quenched with water. After the resultant suspension was poured into a reparatory funnel, the organic phase was washed well with water. The organic phase was then collected and stripped to dryness. The resultant waxy solid was loaded onto a reverse phase silica column, which was eluted with a gradient of dichloromethane in acetonitrile (i.e., 1 L of 30% DCM in ACN, 1 L of 35% DCM in ACN, 2 L of 40% DCM in ACN, and 1 L of 50% DCM in ACN). After the product-containing fractions were combined, the solvent was removed by evaporation. The residue was dried under high vacuum overnight to give 1.552 g (89% yield) of the title compound (96% pure by HPLC).

Synthesis of Polymer 5

600 mg of 2,3,4,5-tetrafluoro-1,6-bis[6-bromo-4,4-di(2-ethylhexyl)-4H-silolo[3,2-b:4,5-b']dithiophene]benzene (0.5256 mmol, 1 eq) was charged into a round bottom flask and purged/flushed with Argon. After 150 ml of dry THF was added to the flask, the solid was dissolved at room temperature. Once a homogeneous solution was obtained, the flask was cooled to −78° C. in a dry ice/acetone bath. The reaction vessel was purged by vacuum and refilled with Argon three times. After stirring for 15 minutes at −78° C., 1.465 ml of n-BuLi (a 2.87 M solution in hexane, 4.205 mmol, 8 eq) was added via a syringe at −78° C. The solution was stirred for 1.5 hours at this temperature. The flask, as well as the remainder of the manipulations, was then protected from light. 5.26 ml of SnMe$_3$Cl (a 1 M solution in hexane, 5.26 mmol, 10 eq) was added to the flask via a syringe. The solution was stirred 20 minutes at −78° C. and then for 2 hours at room temperature. The reaction mixture was quenched with water and extracted with ether. The organic layer was washed with water, dried over MgSO$_4$, filtered, and stripped to dryness. HPLC (60:40 ACN:DCM) showed ~95% conversion to the bis-tin intermediate (23.239 minutes at room temperature), which was dried under high vacuum overnight.

683 mg of the above bis-tin intermediate were collected and charged into a round bottom flask along with 381 mg of Compound 2 (0.471 mmol, 0.95 eq) prepared in Example 2, 21 mg of tris(dibenzylidene-acetone)-dipalladium (0) (Pd (dBA)$_2$, 5% by mole) and 7 mg of tri-(o-tolyl)phosphine (tri-o-toly, 5% by mole). The reaction vessel was purged of air and refilled with Argon three times. 150 ml of degassed toluene was added to the flask via a syringe. The reaction mixture was then heated to 95° C. for four days. 8 g of a metal scavenger (i.e., sodium diethyldithiocarbamate trihydrate) was dissolved in 100 ml of DI water and added to the flask. The resultant suspension was stirred vigorously at 90° C. overnight. The suspension was cooled to room temperature and poured into a separatory funnel. The organic phase was washed well with water and isolated. This solution was poured into 1500 ml of MeOH at room temperature. The resultant suspension was filtered and the solid thus obtained was collected into a soxhlet thimble. A sample of this crude material was tested by GPC, which showed that the material has a M$_n$ of 32,107, a M$_w$ of 105,518, and a PD of 3.286. This thimble was extracted with MeOH overnight (16 hours), extracted with acetone for 8 hours, extracted with hexane for 16 hours, extracted with DCM for 8 hours, and extracted with chloroform for 16 hours. The chloroform fraction was dried and isolated. GPC of this chloroform fraction showed a M$_n$ of

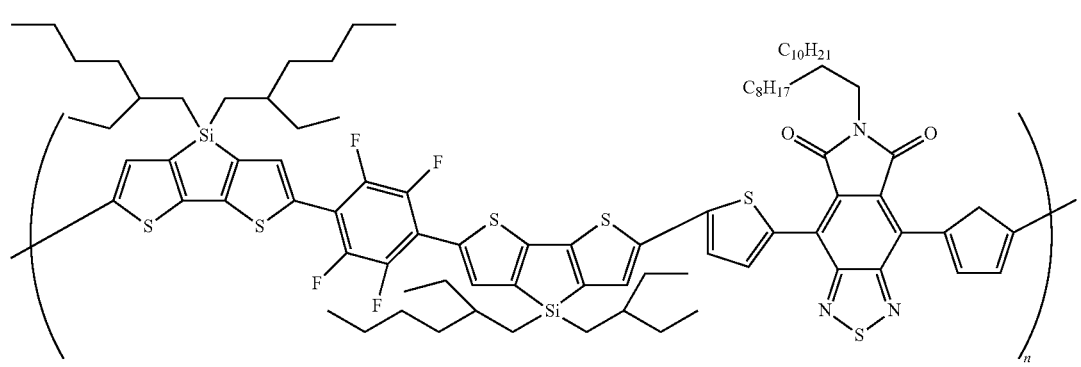

(Polymer 5)

45,999, a $M_w$, of 113,896, and a PD of 2.53. Drying the chloroform fraction gave 627 mg of Polymer 5 (81.5% yield based on the amount of di-bromo compound above used in the synthesis).

EXAMPLE 6

Synthesis of Polymer 6

Synthesis of 5-(2-Ethylhexyl)maleimide

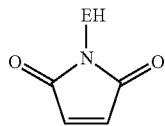

To a dry 500 mL round bottom flask equipped with a stir bar was added 5.4 g (55 mmol) maleic anhydride. 150 mL of toluene was added to the flask followed by slow addition of 8.20 mL (50.05 mmol) ethylhexylamine in an additional 100 mL of toluene using a pressure equalizing dropping funnel. The maleic anhydride dissolved completely in the solution during the addition. After the addition was complete, the reaction mixture was allowed to stir for 2.5 hours. During this time, a hot plate with an oil bath and a temperature feedback feature was set to 80° C. After the 2.5 hours, 12.4 g (55 mmol) of zinc bromide and 15.7 mL (74.8 mmol) hexamethyldisilazane were added to the flask, which was then dropped into the oil bath at 80° C. for an additional 2.5 hours. A white precipitate was formed. The solution was cooled and left to stir overnight. The reaction mixture was then poured into 200 mL of 0.5 M HCl (diluted from 8.3 mL of conc. HCl). After the organic layer was separated, the aqueous layer was extracted twice with ethyl acetate. The combined organic layer was washed twice with saturated aqueous sodium bicarbonate, once with brine, and dried over magnesium sulfate. After the magnesium sulfate was removed by filtration, the filtrate was concentrated by rotary evaporation and left on high vacuum overnight to produce a clear, slightly tan oil in quantitative yield.

Synthesis of 5-(2-Ethylhexyl)-pyrrolo[3,4-f]-4,7-bis(2-bromo-thiophene)-2,1,3-benzothiadiazole-5,7(6H)-dione (Compound 3)

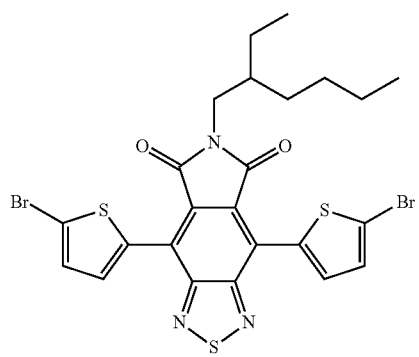 [SMILES: CCCCC(CC)CN1C(=O)c2c(c(-c3ccc(Br)s3)c3nsnc3c2-c2ccc(Br)s2)C1=O]

A hot plate with an oil bath and a temperature feedback was set to 105° C. To a dry 250 mL round bottom flask containing a stir bar was added 1 g (2.154 mmol) of 4,6-bis(5-bromo-2-thienyl)thieno[3,4-c][1,2,5]thiadiazole and 1.8 g (8.616 mmol) of 5-(2-ethylhexyl)maleimide. The flask was capped and purged three times with alternating argon/vacuum cycles. After 80 mL of anhydrous toluene was added to the flask, the reaction mixture was dropped into an oil bath at 105° C. overnight (not refluxing). The reaction was allowed to continue at 105° C. until the blue color of the starting material was completely gone. Once the Diels-Alder cyclization was complete, the reaction was cooled to room temperature. 2.655 g (11.85 mmol, 77% max) of meta-chloroperoxy-benzoic acid was added to the flask in one portion. The reaction was allowed to stir at room temperature for one additional night and concentrated. The residue was purified by column chromatography using 9:1 hexane:ethyl acetate as eluting solvents. The desired product was the first major fraction to elute. 685 mg (49.7% yield) of the title compound was obtained as a bright red product.

Synthesis of Polymer 6

A hot plate with an oil bath and a temperature feedback feature was set to 120° C. To a 100 mL round bottom containing a stir bar and 2,3,4,5-tetrafluoro-1,6-bis[6-trimethyltin-4,4-di(2-ethylhexyl)-4H-silolo[3,2-b:4,5-b']dithiophene] benzene prepared in Example 5 (563.7 mg, 0.4306 mmol, 96.5% purity by HPLC) were added 250 mg (0.3910 mmol) of Compound 3 prepared above, 9.86 mg (0.0108 mmol) of a palladium catalyst, and 26.2 mg (0.0861 mmol) of a phosphorous ligand. The flask was fitted with a condenser and purged three times with alternating argon/vacuum cycles. A syringe was used to add anhydrous toluene through the septa on the condenser. The flask was dropped into the oil bath at 120° C. and allowed to stir for 4 days. Precipitate and a deep green color were observed within a few hours. After the temperature of the reaction was decreased to 80° C., 7.76 g (34.45 mmol) of sodium diethyldithiocarbamate trihydrate in 40 mL of deionized water was added to the reaction mixture, which was, allowed to be stirred for one additional day. The reaction was then removed from heat and the organic phase was allowed to be separated from the aqueous phase. After the aqueous layer was removed, the organic phase was washed with deionized water twice and then poured into 700 mL of methanol to form a precipitate. The suspension was filtered to give a crude polymer ($M_n$: 23,217, PD: 3.06), which was fractionated in a Soxlet apparatus using methanol (full day), acetone (8 hours), hexane (overnight), DCM (8 hours), Chloroform (overnight), and chlorobenzene (8 hours). The remaining undissolved polymer material was extracted with o-dichlorobenzene at 160° C. overnight. The ODCB extract was poured into 700 mL of methanol to form a precipitate, which was filtered to give 296 mg (51.7% yield) of Polymer 6 ($M_n$: 55,374, PD: 1.9).

EXAMPLE 7

Measurements of Physical Properties of Polymers 1-6

The HOMO/LUMO values of Polymers 1-6 were measured by cyclic voltammetry. Cyclic voltammetry measurements were performed by drop casting the polymer from an o-dichlorobenzene solution (1 mg/mL) onto a 3.0 mm diameter glassy carbon electrode. The counter electrode was a platinum wire. The reference electrode was $Ag/AgNO_3$ (0.01M) in 0.1M $nBu_4NPF_6/CH_3CN$ which contacted the electrolyte solution using a porous vycor salt bridge filled with electrolyte. The electrolyte solution was 0.1M $nBu_4NPF_6$ in acetonitrile. The acetonitrile was Chromasolve grade from Sigma-Aldrich used as received. All electrochemistry was done under high purity argon atmosphere using a BAS 100B/W electrochemical analyzer. The scan rate was 20 mV/s with the scan initiated in the oxidative direction. Ferrocene, purified by sublimation, was used as an external reference to convert potentials to the SCE scale. The vacuum level of SCE is assumed to be −4.7 eV. The results are summarized in Table 1 below.

TABLE 1

| Photoactive Polymer | HOMO (eV) | LUMO (eV) | $E_g$ (ec)[a] (eV) | $E_g$ (opt, soln)[b] (eV) | $E_g$ (opt, film)[c] (eV) |
| --- | --- | --- | --- | --- | --- |
| Polymer 1 | −5.4 | −3.9 | 1.50 | 1.57 | — |
| Polymer 2 | −5.55 | −3.97 | 1.58 | 1.59 | — |
| Polymer 3 | −5.36 | −3.9 | 1.46 | 1.57 | — |
| Polymer 4 | −5.43 | −3.93 | 1.50 | 1.73 | 1.42 |
| Polymer 5 | −5.56 | −3.91 | 1.65 | 1.53 | 1.50 |
| Polymer 6 | −5.46 | −3.95 | 1.51 | 1.51 | 1.50 |

[a]Bandgap obtained from the cyclic voltammetry measurements described above.
[b]Bandgap obtained from UV-Vis measurements of photoactive polymer solutions.
[c]Bandgap obtained from UV-Vis measurements of photoactive polymer films.

UV-Visible spectra of Polymers 1-6 were acquired on a Perkin-Elmer Lambda35 spectro-photometer. Stock samples of the polymers in o-dichlorobenzene (o-DCB) at a 1 mg/mL concentration were diluted with o-DCB to prepare solutions that gave maximum peak intensity between 0.70 and 0.95 absorbance units. The path length of the quartz cuvettes was 1 cm. The instrument was used in double beam mode with a reference 1 cm quartz cuvette containing o-DCB. HPLC grade (Chromosolv brand from Sigma-Aldrich) o-DCB was used. Spectra were taken at ambient temperature. The results are summarized in Table 2 below.

TABLE 2

| Photoactive Polymer | $\lambda_{max}$ (nm) | $E_g$ (opt, soln) (eV) |
| --- | --- | --- |
| Polymer 1 | 418, 630 | 1.57 |
| Polymer 2 | 470, 649 | 1.59 |
| Polymer 3 | 446, 662 | 1.57 |
| Polymer 4 | 382, 604 | 1.73 |
| Polymer 5 | 479, 637 | 1.53 |
| Polymer 6 | 487, 680 | 1.51 |

EXAMPLE 8

Fabrication of Photovoltaic Cells Using Photoactive Polymers 2 and 4-6

Photoactive polymers 2 and 4-6 were used to fabricate inverted organic photovoltaic cells containing a glass substrate with a transparent pre-patterned indium tin oxide (ITO) bottom electrode, a hole blocking layer on top of the ITO electrode, a photoactive layer on top of the hole blocking layer, a hole carrier layer on top of the photoactive layer, and a top silver electrode. The hole blocking layer contained a crosslinked polyamine and the hole carrier layer contained a thiophene polymer in the HIL family available from Air Products and Chemicals, Inc. The photoactive layer was formed from a blend of a photoactive polymer and PCBM (1:2 by weight) dissolved in 1,2-dichlorobenzene at a concentration of 0.6% by weight by using a blade-coating technique. The photoactive polymer solution was stirred at 80° C. for at least 12 hours before coating. During the blade-coating process, the solution was kept under stirring at 80° C. while the blade-coater temperature was maintained at 50° C. The thickness of the photoactive layer was adjusted by the blade speed and the volume of solution deposited.

The current density-voltage characteristics of the devices were measured as described in Waldauf et al., Appl. Phys. Lett., 89, 233517 (2006). The results are summarized in Table 3 below.

TABLE 3

| Photovoltaic Cell | Conversion Efficiency (%) | Fill Factor (%) | Open-Circuit Voltage (V) | Short-Circuit Current (mA/cm$^2$) |
| --- | --- | --- | --- | --- |
| Cell having polymer 2 | .75 | .55 | .940 | 1.5 |
| Cell having polymer 4 | 1.5 | .48 | .840 | 5 |
| Cell having polymer 5 | 3.6 | .54 | .850 | 7.6 |
| Cell having polymer 6 | 5.0 | .60 | .780 | 14 |

Other embodiments are within the scope of the following claims.

What is claimed is:
1. An article, comprising:
a first electrode,
a second electrode, and
a photoactive layer disposed between the first and second electrodes, the photoactive layer comprising a polymer including a first monomer repeat unit, the first monomer repeat unit comprising a moiety of formula (1):

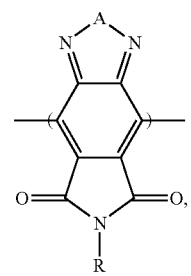

in which A is S; and R is H, $C_1$-$C_{24}$ alkyl optionally containing oxygen, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl; wherein the article is configured as a photovoltaic cell.

2. The article of claim 1, wherein R is $C_1$-$C_{24}$ alkyl optionally containing oxygen and optionally substituted with halo or $C_1$-$C_{24}$ alkoxy.

3. The article of claim 2, wherein R is $C_8H_{17}$, $C_{12}H_{25}$, or $C_{20}H_{41}$.

4. The article of claim 1, wherein the polymer further comprises a second monomer repeat unit different from the first monomer repeat unit.

5. The article of claim 4, wherein the second monomer repeat unit comprises a moiety selected from the group consisting of the moieties of formulas (2)-(23):

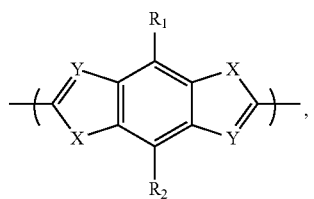
(2)

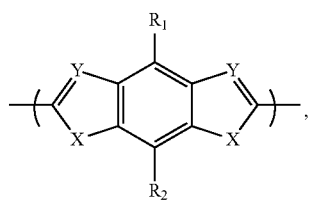
(3)

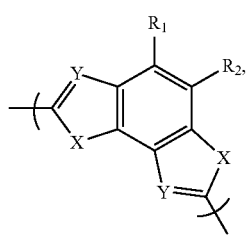
(4)

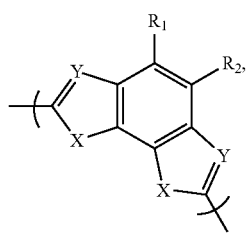
(5)

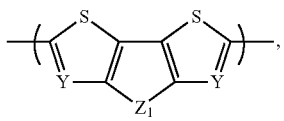
(6)

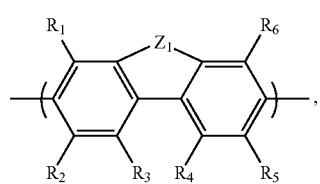
(7)

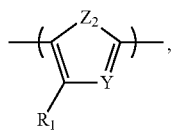
(8)

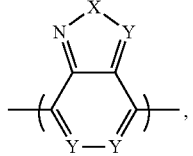
(9)

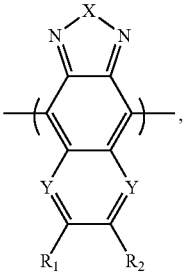
(10)

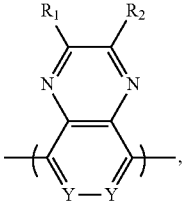
(11)

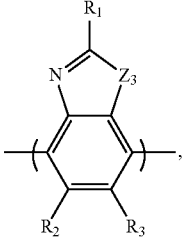
(12)

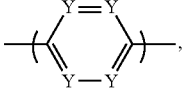
(13)

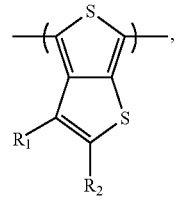
(14)

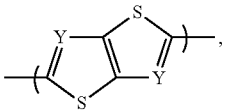
(15)

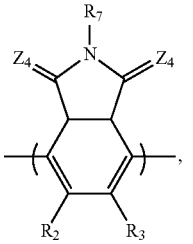
(16)

-continued (17)

(18)

(19)

(20)

(21)

(22)

(23)

wherein
each X, independently, is O, S, or Se;
each Y, independently, is N or C($R_a$);
$Z_1$ is N($R_a$), S, Si($R_aR_b$), or C($R_aR_b$);
$Z_2$ is O, S, Se, N($R_a$), Si($R_aR_b$), or C($R_aR_b$);

$Z_3$ is O, S, or N($R_a$);
each $Z_4$, independently, is $CH_2$, O, or S;
each of $R_1$, $R_2$, $R_3$, $R_4$, $R_5$, and $R_6$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$;
$R_7$ is H, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $COR_c$ or $COOR_c$;
each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl;
each $R_b$, independently, is H, halo, $C_1$-$C_{24}$ alkyl, aryl, heteroaryl, $C_3$-$C_{24}$ cycloalkyl, or $C_3$-$C_{24}$ heterocycloalkyl; and
each $R_c$, independently, is H, $C_1$-$C_{24}$ alkyl, aryl, heteroaryl, $C_3$-$C_{24}$ cycloalkyl, or $C_3$-$C_{24}$ heterocycloalkyl.

6. The article of claim 5, wherein the second monomer repeat unit comprises a moiety of formula (2), a moiety of formula (6), or a moiety of formula (8).

7. The article of claim 6, wherein the second monomer repeat unit comprises a moiety of formula (2), in which each X is S, each Y is C($R_a$), and each of $R_1$ and $R_2$, independently, is $OR_c$ or $COOR_c$.

8. The article of claim 7, wherein each $R_a$ is H and each $R_c$, independently, is $C_1$-$C_{24}$ alkyl.

9. The article of claim 6, wherein the second monomer repeat unit comprises a moiety of formula (6), in which each Y is C($R_a$) and $Z_1$ is Si($R_aR_b$).

10. The article of claim 9, wherein each $R_a$, independently, is H or $C_1$-$C_{24}$ alkyl, and $R_b$ is $C_1$-$C_{24}$ alkyl.

11. The article of claim 6, wherein the second monomer repeat unit comprises a moiety of formula (8), in which Y is C($R_a$) and $Z_2$ is S.

12. The article of claim 11, wherein $R_1$ is $C_1$-$C_{24}$ alkyl and $R_a$ is $C_1$-$C_{24}$ alkyl.

13. The article of claim 6, wherein the polymer further comprises a third monomer repeat unit different from the first and second monomer repeat units.

14. The article of claim 13, wherein the third monomer repeat unit comprises a moiety of formula (8):

(8)

in which Y is N or C($R_a$); $Z_2$ is O, S, Se, N($R_a$), Si($R_aR_b$), or C($R_aR_b$); $R_1$ is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$ or $COOR_c$; each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl; $R_b$ is H, halo, $C_1$-$C_{24}$ alkyl, aryl, heteroaryl, $C_3$-$C_{24}$ cycloalkyl, or $C_3$-$C_{24}$ heterocycloalkyl; and $R_1$ is H, $C_1$-$C_{24}$ alkyl, aryl, heteroaryl, $C_3$-$C_{24}$ cycloalkyl, or $C_3$-$C_{24}$ heterocycloalkyl.

15. The article of claim 14, wherein the third monomer repeat unit comprises a moiety of formula (8), in which Y is C($R_a$) and $Z_2$ is S.

16. The article of claim 15, wherein, in the moiety of formula (8) in the third monomer repeat unit, $R_1$ is H and $R_a$ is H.

17. The article of claim 16, wherein the polymer is one of polymers 1-4.

18. The article of claim 13, wherein the polymer further comprises a fourth monomer repeat unit different from the first, second, and third monomer repeat units.

19. The article of claim 18, wherein the fourth monomer repeat unit comprises a moiety of formula (13):

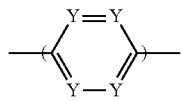

in which each Y, independently, is N or $C(R_a)$, each $R_a$, independently, being H, halo, $C_1$-$C_{24}$ alkyl, aryl, heteroaryl, $C_3$-$C_{24}$ cycloalkyl, or $C_3$-$C_{24}$ heterocycloalkyl.

20. The article of claim 19, wherein the fourth monomer repeat unit comprises a moiety of formula (13), in which each Y is $C(R_a)$.

21. The article of claim 20, wherein, in the moiety of formula (13) in the fourth monomer repeat unit, each $R_a$ is F.

22. The article of claim 21, wherein the polymer is polymer 5 or polymer 6.

23. A polymer, comprising:
a first monomer repeat unit comprising a moiety of formula (1):

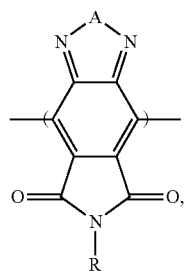

wherein

A is S; and

R is H, $C_1$-$C_{24}$ alkyl optionally containing oxygen, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, or heteroaryl.

24. The polymer of claim 23, wherein R is $C_1$-$C_{24}$ alkyl optionally containing oxygen and optionally substituted with halo or $C_1$-$C_{24}$ alkoxy.

25. The polymer of claim 24, wherein R is $C_8H_{17}$, $C_{12}H_{25}$, or $C_{20}H_{41}$.

26. The polymer of claim 22, wherein the polymer further comprises a second monomer repeat unit different from the first monomer repeat unit.

27. The polymer of claim 26, wherein the second monomer repeat unit comprises a moiety selected from the group consisting of the moieties of formulas (2)-(23):

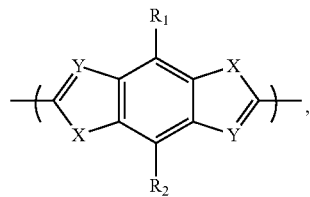

(2)

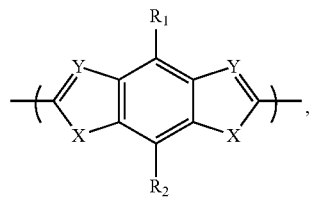

(3)

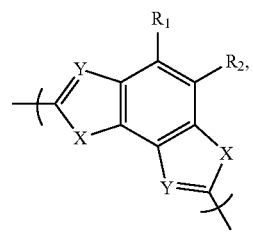

(4)

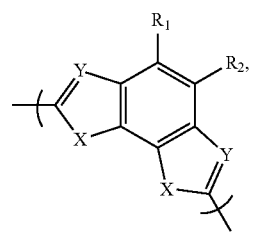

(5)

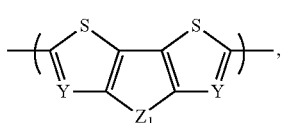

(6)

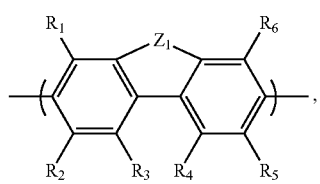

(7)

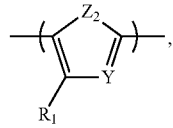

(8)

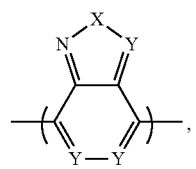

(9)

-continued
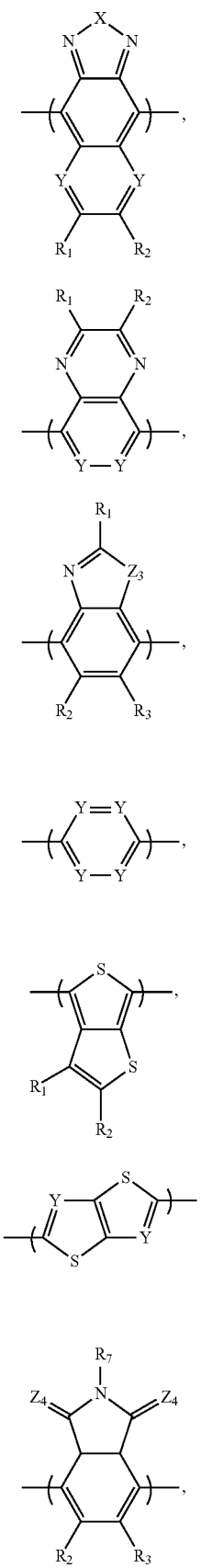
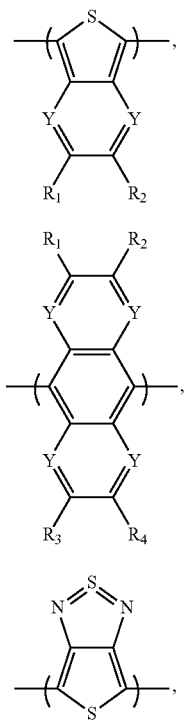
wherein
each X, independently, is O, S, or Se;
each Y, independently, is N or C($R_a$);
$Z_1$ is N($R_a$), S, Si($R_aR_b$), or C($R_aR_b$);
$Z_2$ is O, S, Se, N($R_a$), Si($R_aR_b$), or C($R_aR_b$);

$Z_3$ is O, S, or $N(R_a)$;

each $Z_4$, independently, is $CH_2$, O, or S;

each of $R_1$, $R_2$, $R_3$, $R_4$, $R_5$, and $R_6$, independently, is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$;

$R_7$ is H, $C_1$-$C_{24}$ alkyl, $C_2$-$C_{24}$ alkenyl, $C_2$-$C_{24}$ alkyllyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $COR_c$, or $COOR_c$;

each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl;

each $R_b$, independently, is H, halo, $C_1$-$C_{24}$ alkyl, aryl, heteroaryl, $C_3$-$C_{24}$ cycloalkyl, or $C_3$-$C_{24}$ heterocycloalkyl; and each $R_c$, independently, is H, $C_1$-$C_{24}$ alkyl, aryl, heteroaryl, $C_3$-$C_{24}$ cycloalkyl, or $C_3$-$C_{24}$ heterocycloalkyl.

28. The polymer of claim 27, wherein the second monomer repeat unit comprises a moiety of formula (2), a moiety of formula (6), or a moiety of formula (8).

29. The polymer of claim 2, wherein the second monomer repeat unit comprises a moiety of formula (2), in which each X is S, each Y is $C(R_a)$, and each of $R_1$ and $R_2$, independently, is $OR_c$ or $COOR_c$.

30. The polymer of claim 29, wherein each $R_a$ is H and each $R_c$, independently, is $C_1$-$C_{24}$ alkyl.

31. The polymer of claim 28, wherein the second monomer repeat unit comprises a moiety of formula (6), in which each Y is $C(R_a)$ and $Z_1$ is $Si(R_aR_b)$.

32. The polymer of claim 31, wherein each $R_a$, independently, is H or $C_1$-$C_{24}$ alkyl, and $R_b$ is $C_1$-$C_{24}$ alkyl.

33. The polymer of claim 28, wherein the second monomer repeat unit comprises a moiety of formula (8), in which Y is $C(R_a)$ and $Z_2$ is S.

34. The polymer of claim 33, wherein $R_1$ is $C_1$-$C_{24}$ alkyl and $R_a$ is $C_1$-$C_{24}$ alkyl.

35. The polymer of claim 28, wherein the polymer further comprises a third monomer repeat unit different from the first and second monomer repeat units.

36. The polymer of claim 35, wherein the third monomer repeat unit comprises a moiety of formula (8):

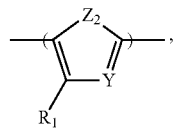

(8)

in which Y is N or $C(R_a)$; $Z_2$ is O, S, Se, $N(R_a)$, $Si(R_aR_b)$, or $C(R_aR_b)$; $R_1$ is H, halo, $C_1$-$C_{24}$ alkyl, $C_2$-$C_{24}$ alkenyl, $C_2$-$C_{24}$ alkynyl, $C_3$-$C_{24}$ cycloalkyl, $C_3$-$C_{24}$ cycloalkenyl, $C_3$-$C_{24}$ heterocycloalkyl, $C_3$-$C_{24}$ heterocycloalkenyl, aryl, heteroaryl, $OR_c$, $COR_c$, or $COOR_c$; each $R_a$, independently, is H, halo, $C_1$-$C_{24}$ alkyl, aryl, heteroaryl, $C_3$-$C_{24}$ cycloalkyl, or $C_3$-$C_{24}$ heterocycloalkyl; $R_b$ is H, halo, $C_1$-$C_{24}$ alkyl, aryl, heteroaryl, $C_3$-$C_{24}$ cycloalkyl, or $C_3$-$C_{24}$ heterocycloalkyl; and $R_c$ is H, $C_1$-$C_{24}$ alkyl, aryl, heteroaryl, $C_3$-$C_{24}$ cycloalkyl, or $C_3$-$C_{24}$ heterocycloalkyl.

37. The polymer of claim 36, wherein the third monomer repeat unit comprises a moiety of formula (8), in which Y is $C(R_a)$ and $Z_2$ is S.

38. The polymer of claim 37, wherein, in the moiety of formula (8) in the third monomer repeat unit, $R_1$ is H and $R_a$ is H.

39. The polymer of claim 38, wherein the polymer is one of polymers 1-4.

40. The polymer of claim 35, wherein the polymer further comprises a fourth monomer repeat unit different from the first, second, and third monomer repeat units.

41. The polymer of claim 40, wherein the fourth monomer repeat unit comprises a moiety of formula (13):

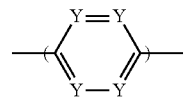

in which each Y, independently, is N or $C(R_a)$, each $R_a$, independently, being H, halo, $C_1$-$C_{24}$ alkyl, aryl, heteroaryl, $C_3$-$C_{24}$ cycloalkyl, or $C_3$-$C_{24}$ heterocycloalkyl.

42. The polymer of claim 41, wherein the fourth monomer repeat unit comprises a moiety of formula (13), in which each Y is $C(R_a)$.

43. The polymer of claim 42, wherein, in the moiety of formula (13) in the fourth monomer repeat unit, each $R_a$ is F.

44. The polymer of claim 43, wherein the polymer is polymer 5 or polymer 6.

* * * * *

UNITED STATES PATENT AND TRADEMARK OFFICE
CERTIFICATE OF CORRECTION

PATENT NO.       : 8,883,954 B2                                        Page 1 of 1
APPLICATION NO.  : 14/049536
DATED            : November 11, 2014
INVENTOR(S)      : Paul Byrne et al.

It is certified that error appears in the above-identified patent and that said Letters Patent is hereby corrected as shown below:

In the Specification
Column 2, line 47,         replace "$COR_{ca}$" with --$COR_c$--
Column 3, lines 66-67,     replace "-$CH_2$-C=$CH_2$, and –C=C-$CH(CH_3)_2$."
                           with -- -$CH_2$-C≡CH, and -C≡C-$CH(CH_3)_2$.--

In the Claims
Claim 5:    Column 50, line 5,    replace "$C_2\bar{\ }C_{24}$" with --$C_2$-$C_{24}$--
            Column 50, line 5,    replace "$C_2\bar{\ }C_{24}$" with --$C_2$-$C_{24}$--
            Column 50, line 9,    replace "$C_2\bar{\ }C_{24}$" with --$C_2$-$C_{24}$--
Claim 14:   Column 50, line 62,   replace "$C_2\bar{\ }C_{24}$" with --$C_2$-$C_{24}$--  replace "$R_1$" with --$R_c$--
Claim 29:   Column 55, line 22,   replace "claim 2, wherein" with --claim 28, wherein--

Signed and Sealed this
Fifth Day of May, 2015

Michelle K. Lee
*Director of the United States Patent and Trademark Office*